United States Patent
Yamada et al.

(10) Patent No.: US 7,279,484 B2
(45) Date of Patent: Oct. 9, 2007

(54) HETEROCYCLIC COMPOUNDS

(75) Inventors: Tatsuhiro Yamada, Kawasaki (JP); Tadakiyo Nakagawa, Kawasaki (JP); Yasuhiro Tanaka, Kawasaki (JP); Kohichi Fujita, Kawasaki (JP); Tomoyuki Tagami, Kawasaki (JP); Yuka Ikenoue, Kawasaki (JP); Shunsuke Fukuda, Kawasaki (JP); Yoshitomo Chujo, Kawasaki (JP); Manabu Suzuki, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 65 days.

(21) Appl. No.: 11/116,310

(22) Filed: Apr. 28, 2005

(65) Prior Publication Data

US 2005/0250796 A1    Nov. 10, 2005

Related U.S. Application Data

(63) Continuation of application No. PCT/JP03/013808, filed on Oct. 29, 2003.

(30) Foreign Application Priority Data

Oct. 30, 2002  (JP) ............... 2002-316900

(51) Int. Cl.
  *A61K 31/519*  (2006.01)
  *C07D 471/04*  (2006.01)
  *C07D 471/14*  (2006.01)
  *A61P 1/04*  (2006.01)
  *A61P 19/02*  (2006.01)

(52) U.S. Cl. ............... 514/264.11; 514/300; 544/279; 546/122

(58) Field of Classification Search ............ 546/122; 544/279; 514/264.11, 300
See application file for complete search history.

(56) References Cited

FOREIGN PATENT DOCUMENTS

| JP | 61-060687 | 3/1986 |
|---|---|---|
| JP | 11-222486 | 8/1999 |
| WO | WO 02/088122 A1 | 11/2002 |

OTHER PUBLICATIONS

Merck Index, 9th Ed., 1976, p. F1-8.*
Souillac, et al., Characterization of Delivery Systems, Differential Scanning Calorimetry, pp. 212-228, in Encyclopedia of Controlled Drug Delivery, 1999, John Wiley & Sons.*

(Continued)

*Primary Examiner*—Mark L. Berch
*Assistant Examiner*—Cecilia M Jaisle
(74) *Attorney, Agent, or Firm*—The Nath Law Group; Gary M. Nath; Susanne M. Hopkins

(57) ABSTRACT

The inventive subject matter relates to compounds, pharmaceutical compositions, and kits containing a heterocyclic compound represented by the formula (I)

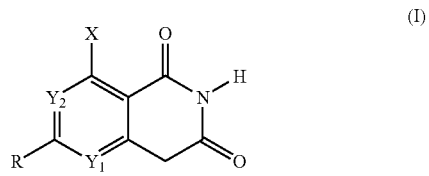

wherein R is an alkyl group optionally having substituent(s) etc., X is an amino group optionally having substituent(s), $Y_1$ and $Y_2$ are nitrogen atoms etc., an isomer or solvate thereof or a pharmaceutically acceptable salt thereof as an active ingredient.

13 Claims, 1 Drawing Sheet

OTHER PUBLICATIONS

Gibson, "Increased gut permeability on Crohn's disease: is TNF the link?" Gut, 2004: 53, 1724-25.*

Giamarellos-Bouboulis, et al., Effective Immunomodulatory Treatment of *Escherichia coli* Experimental Sepsis with Thalidomide, Antimicrobial Agents and Chemotherapy, Aug. 2003, p. 2445-2449.*

"Access to Anti- TNF-α Therapies for Adults with Inflammatory Arthritis," Implementation of NICE Guidance on use of Anti-TNF-α Therapies for Adults with Rheumatoid Arthritis, Jun. 2005, pp. 1-8, the NICE Report.*

Waldman, "Targeting the interleukin-15/interleukin-15 receptor system in inflammatory autoimmune diseases," Arthritis Research & Therapy, vol. 6, No. 4, 2004, pp. 174-177.*

Jiménez, "Infliximab in the Treatment of Severe Ulcerative Colitis," Rev. esp. enfirm. Dig., vol. 2004, No. 2, Feb. 2004, 4 pages.*

Medical dictionary, University of Newcastle upon Tyne, http://cancerweb.ncl.ac.uk/cgi-bin/omd?query=prophylaxis&action=Search+OMD, 2005.*

Understanding Animal Research in Medicine, Aug. 2004, http://www.rds-online.org.uk/pages/page.asp?i_PageID=141&l_ToolbarID=3.*

.Waterston, et al., Cancer Therapy, vol. 2, pp. 131-148, 2004.*

Elnagdi, M.H. et al. "Activated Nitriles in Heterocyclic Synethsis: A New Procedure for the Synthesis of Pyrimidine Derivatives", *J. Chem. Soc. Perkin Trans.*, vol. I pp. 2667-2670, 1982.

\* cited by examiner

HETEROCYCLIC COMPOUNDS

This application is a Continuation of International Application No. PCT/JP2003/013808, filed Oct. 29, 2003 and is based on, and claims priority to, Japanese Patent Application No. 2002-316900, filed Oct. 30, 2002, the contents of which are hereby incorporated by reference in their entirety.

TECHNICAL FIELD

The present invention relates to novel heterocyclic compounds. More particularly, the present invention relates to heterocyclic compounds useful for treating various inflammatory diseases.

BACKGROUND ART

It has been recently clarified that TNF-α is an inflammatory cytokine produced by macrophages, macrophage-like cells (Kupffer's cells and microglia), neutrophiles, basophils, eosinophils, lymphocytes, NK cells, LAK cells, mast cells, bone marrow cells, fibroblasts, astrocytes, keratinocytes and the like, and is deeply involved in the onset and pathology of many diseases. The potential establishment of a new treatment method for controlling excess TNF-α has been reported (See, e.g., Black et al., *Annual Reports in Medicinal Chemistry*, USA, No. 32, pp. 241-250 (1997)).

As regards the correlation between TNF-α and pathology, for example, systemic inflammatory response syndromes including sepsis, septic shock and multiple organ dysfunction syndrome (MODS) are considered to be caused by abnormal production of inflammatory cytokines such as TNF-α, interleukin 1β, interleukin 6 and the like, and neutralization of TNF-α suppresses increase in blood interleukin 1β and blood interleukin 6 (See, e.g., Tracey et al., *Nature*, UK, No. 330, pp. 662-664 (1987)).

Moreover, a report has documented that insulin resistance induced by obesity can be improved in TNF-α defective animals, which suggests a relationship between TNF-α and non-insulin dependent diabetes mellitus (NIDDM) (See, Uysal et al., *Nature*, UK, No. 389, pp. 610-614 (1997)).

It has also been clarified in the field of autoimmune diseases that TNF-α affects nerve cells and oligodendrocytes, and plays the role of an effector in neurodegeneration and demyelination (e.g., Suzumura, *Igakuno Ayumi*, Ishiyaku Publishers, Inc., No. 185, pp. 931-935 (1998)).

Furthermore, detection of a large amount of TNF-α in the synovial fluid of patients with rheumatoid arthritis has also been reported (e.g., Saxne et al., *Arthritis & Rheumatism*, US, No. 31, pp. 1041-1045 (1998)).

Besides these, the involvement of TNF-α in the etiology of Crohn's disease, fulminant hepatitis, cachexia, bone absorption disease, cardiac infarction, allergic disease and adult respiratory distress syndrome has been pointed out.

Since TNF-α is deeply involved in the onset and aggravation of various diseases, inhibition of the action of TNF-α is considered to enable treatment of those diseases.

While steroid hormone drugs and non-steroidal antiinflammatory agents are currently utilized for some inflammatory diseases, since they act at various sites and fail to show a specific TNF-α inhibitory action, they may induce harmful side effects. Particularly, the side effects of steroidal agents have themselves become medical problems. An in vitro test report exists, which teaches that a pharmaceutical agent having a phosphodiesterase inhibitory action inhibits TNF-α production. However, its efficacy in living organisms is very weak, to the point that clinical application is considered to be difficult (See, Suzumura, *Igakuno Ayumi*, Ishiyaku Publishers, Inc., No. 185, pp. 931-935 (1998)). Furthermore, while a treatment using a TNF-α antibody or a soluble TNF-α receptor, which are peptidic polymer compounds, achieved a superior clinical effect in rheumatoid arthritis, Crohn's disease and the like, its treatment effect is not persistent for a long term except in certain patients.

In view of the present situation, the development of a pharmaceutical agent for the prophylaxis or treatment of various diseases considered to be attributable to abnormal TNF-α production, which agent specifically inhibits TNF-α production and which shows a superior treatment effect in living organisms, has been desired.

As a heterocyclic compound, for example, a compound represented by

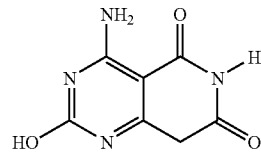

has been reported (See, Mohamed Hilmy Elnagdi et al., *Journal of Chemical Society Perkin*) Transaction I, UK, pp. 2667-2670 (1982)), but this reference does not contain any description relating to biological activity. In addition, a compound represented by

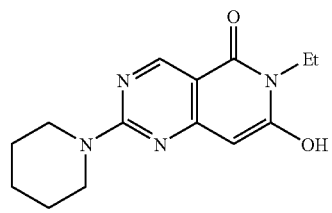

(Et: ethyl group)

has been reported (e.g., JP-A-61-60687), but this reference only describes its activity as a herbicide and does not contain any description relating to TNF-α production inhibitory action.

It is therefore an object of the present invention to provide novel compounds having TNF-α inhibitory activity, methods of using said TNF-α inhibitors, and pharmaceutical compositions and uses of the novel compounds.

DISCLOSURE OF THE INVENTION

The present inventors have conducted intensive studies in an attempt to achieve the above-mentioned objects and succeeded in developing novel compounds having a TNF-α production inhibitory action. We have found that these compounds have superior TNF-α production inhibiting ability in living organisms and are effective in an inflammatory disease model, resulting in the completion of the present invention. Accordingly, the present invention provides the following:

(1) A heterocyclic compound represented by the formula (I)

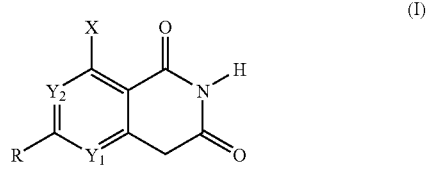

wherein R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s),
a heterocyclic-alkyl group optionally having substituent(s),
A-B-
wherein A is an alkyl group optionally having substituent(s), a cycloalkyl group optionally having substituent(s), an aryl group optionally having substituent(s), a heteroaryl group optionally having substituent(s) or a heterocyclic group optionally having substituent(s), and
B is an oxygen atom or a sulfur atom, and

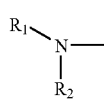

(II)

wherein $R_1$ and $R_2$ are the same or different and each is:
a hydrogen atom,
an alkyl group optionally having substituent(s),
a cycloalkyl group optionally having substituent(s),
an aryl group optionally having substituent(s),
a heteroaryl group optionally having substituent(s), or
a heterocyclic group optionally having substituent(s);
X is an amino group optionally having substituent(s); and
$Y_1$ and $Y_2$ is each a nitrogen atom or a —CH— moiety provided that $Y_1$ and $Y_2$ are not —CH— moieties at the same time, an isomer or solvate thereof or a pharmaceutically acceptable salt thereof.
(2) The heterocyclic compound of formula (I), as shown in (1) above, wherein
$Y_1$ and $Y_2$ are nitrogen atoms,
an isomer or solvate thereof or a pharmaceutically acceptable salt thereof.
(3) The heterocyclic compound of formula (I), as shown in (1) above, wherein R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s), and
a heterocyclic-alkyl group optionally having substituent(s),
an isomer or solvate thereof or a pharmaceutically acceptable salt thereof.
(4) The heterocyclic compound of formula (I), as shown in (1) above, wherein
R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s), and
a heterocyclic-alkyl group optionally having substituent(s); and
$Y_1$ and $Y_2$ are nitrogen atoms,
an isomer or solvate thereof or a pharmaceutically acceptable salt thereof.
(5) The heterocyclic compound of formula (I), as shown in (1) above, wherein
R is any of:
an alkyl group optionally having substituent(s),
a cycloalkylalkyl group optionally having substituent(s),
an aryl group optionally having substituent(s),
an aralkyl group optionally having substituent(s), and
a heteroarylalkyl group optionally having substituent(s),
an isomer or solvate thereof or a pharmaceutically acceptable salt thereof.
(6) The heterocyclic compound of formula (I), as shown in (1) above, wherein
R is any of:
an alkyl group optionally having substituent(s),
a cycloalkylalkyl group optionally having substituent(s),
an aryl group optionally having substituent(s),
an aralkyl group optionally having substituent(s), and
a heteroarylalkyl group optionally having substituent(s); and
$Y_1$ and $Y_2$ are nitrogen atoms,
an isomer or solvate thereof or a pharmaceutically acceptable salt thereof.
(7) The heterocyclic compound of formula (I), as shown in (1) above, wherein R is any of:
an alkyl group optionally having substituent(s),
a cycloalkylalkyl group optionally having substituent(s),
an aryl group optionally having substituent(s),
an aralkyl group optionally having substituent(s), and
a heteroarylalkyl group optionally having substituent(s);
$Y_1$ and $Y_2$ are nitrogen atoms; and
X is an amino group,
an isomer or solvate thereof or a pharmaceutically acceptable salt thereof.
(8) The heterocyclic compound of formula (I), as shown in (1) above, wherein R is an aralkyl group optionally having substituent (s);
$Y_1$ and $Y_2$ are nitrogen atoms; and
X is an amino group,
an isomer or solvate thereof or a pharmaceutically acceptable salt thereof.
(9) A pharmaceutical composition comprising:
the heterocyclic compound as shown in any of (1)-(8) above, or an isomer or solvate thereof, or a pharmaceutically acceptable salt thereof as an active ingredient.
(10) The heterocyclic compound as shown in any of (1)-(8) above, or an isomer or solvate thereof, or a pharmaceutically acceptable salt thereof, which is a TNF-α production inhibitor.
(11) The pharmaceutical composition as shown in (9) above, which is used for the prophylaxis or treatment of a disease for which inhibition of the production of TNF-α is effective.
(12) The pharmaceutical composition as shown in (9) above, which is used for the prophylaxis or treatment of at least one disease selected from the group consisting of Crohn's disease, ulcerative colitis, sepsis, rheumatoid arthritis and autoimmune disease.

The present invention further relates to a method of preventing or treating a disease for which inhibition of the production of TNF-α is effective, which comprises administering an effective amount of the compound represented by the formula (I) to a patient in need thereof, and to the use of the compound represented by the formula (I) for the production of a pharmaceutical agent for the prophylaxis or treatment of a disease for which inhibition of the production of TNF-α is effective. Moreover, the present invention provides a commercial package comprising an effective amount of the compound represented by the formula (I) for the prophylaxis or treatment of a disease for which inhibition of the production of TNF-α is effective, and optionally provides instructions for the use of said compound for the prophylaxis or treatment of a disease for which inhibition of the production of TNF-α is effective.

DETAILED DESCRIPTION OF THE INVENTION

Figure 1:
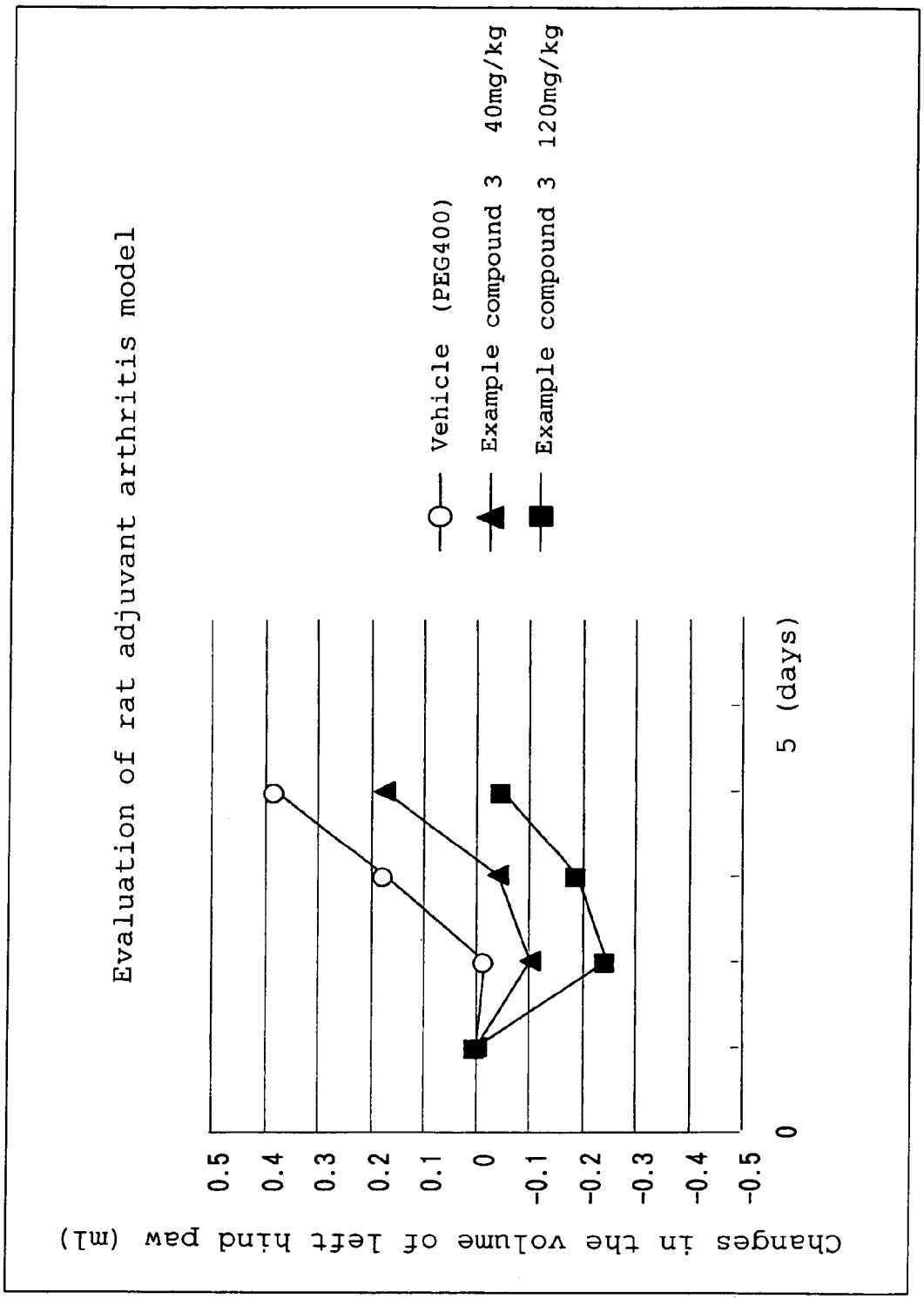
FIG. 1 is a graph showing the results of an efficacy test for suppression of joint swelling in a rat adjuvant arthritis model, wherein changes in the volume of the left hindpaw injected with an adjuvant was measured. The administration of the compound of the present invention remarkably suppressed the swelling of the joints.

In the present invention, the term "disease for which inhibition of the production of TNF-α is effective" means a disease for which increase in the TNF-α activity is inconvenient, and in which inhibition of the TNF-α activity is expected to alleviate the manifestation and/or progress of the disease. To be specific, the presence of TNF-α in the patients affected by the disease has been shown or suspected to be the cause of the physiopathology of the disease or a factor conducive to the aggravation of the disease. Examples of such disease include, but not limited to, septic shock, sepsis, endotoxin shock, hemodynamic shock, post ischemic reperfusion injury, meningitis, psoriasis, congestive heart failure (congestive cardiomyopathy), fibrosis, hepatitis, non-insulin dependent diabetes mellitus (NIDDM), graft rejection, graft versus host disease, cancer, cachexia, autoimmune diseases (systemic lupus erythematosus, rheumatic disease, allergy, multiple sclerosis, autoimmune uveitis, nephritic syndrome, type I diabetes mellitus (IDDM) etc.), arthritis (rheumatoid arthritis, rheumatoid spondylitis, steoarthrosis, other arthritis), inflammatory bone diseases, bone absorption diseases, Behcet's syndrome, infectious diseases (opportunistic infectious disease in AIDS, cerebral malaria, mycobacterial infectious disease etc.), Crohn's disease, ulcerative colitis, ENL in leprosy, radiation damage, damage of aircell by high oxygen and the like, particularly, Crohn's disease, ulcerative colitis, sepsis, rheumatoid arthritis, autoimmune disease and the like.

In the present invention, the term "inhibition of TNF-α production" is not particularly limited to any action mechanism as long as TNF-α secretion from a TNF-α producing cell such as macrophage, macrophage-like cell (Kupffer's cell and microglia), neutrophile, basophils, eosinophil, lymphocyte, NK cell, LAK cell, mast cell, bone marrow cell, fibroblast, astrocyte, keratinocyte and the like can be inhibited, wherein the expression may be inhibited at a gene level, or the expression may be inhibited at a protein level. The inhibition of TNF-α production can be confirmed by a known technique such as measurement of a cell culture supernatant or serum by sandwich ELISA (See, e.g., *Meneki Jikken Sousahou I-II*, Shunsuke Migita, Susumu Konda, Tasuku Honjo, Toshiyuki Hamaoka ed., Nankodo (1995)) and the like.

In the present invention, the term "target" to which the heterocyclic compound represented by the formula (I) is administered is not particularly limited and includes mammals inclusive of human (e.g., human, monkey, mouse, rat, guinea pig, rabbit, cow, horse, sheep, goat, etc.), tissue and cells obtained from the mammal (including tissue, cells cultured after harvesting, tissue reconstructed using them and the like) and the like, with preference given to human and tissue and cells obtained from human.

In the present invention, the animal species of the "patients" is not particularly limited as long as it is the aforementioned mammal including human, with preference given to human. Moreover, the "patients" includes an individual affected with the disease and an individual potentially affected with the disease in the future.

The present invention provides novel use of a heterocyclic compound represented by the formula (I), particularly use as a pharmaceutical agent. More particularly, a TNF-α production inhibitor and a pharmaceutical composition for the prophylaxis or treatment of various diseases considered to be caused by abnormal production and activity of TNF-α.

The definition of each functional group in the present specification is explained in detail in the following.

The term "alkyl group optionally having substituent(s)" means an alkyl group optionally substituted by 1 to 5 substituents. Here, the term "alkyl group" means a straight chain or branched alkyl group having 1 to 10 carbon atoms, such as methyl group, ethyl group, n-propyl group, isopropyl group, n-butyl group, isobutyl group, sec-butyl group, tert-butyl group, n-pentyl group, isopentyl group, tert-pentyl group, neopentyl group, 2-pentyl group, 3-pentyl group, n-hexyl group, 2-hexyl group, n-heptyl group, 2-heptyl group, n-octyl group, 2-octyl group, n-nonanyl group, 2-nonanyl group, n-decanyl group, 2-decanyl group and the like. As the "substituent", halogen atom, hydroxyl group, alkoxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "cycloalkyl group optionally having substituents" means a cycloalkyl group optionally substituted by 1 to 5 substituents. Here, the "cycloalkyl group" means a cyclic alkyl group having 3 to 7 carbon atoms, such as cyclopropyl group, cyclobutyl group, cyclopentyl group, cyclohexyl group, cycloheptyl group and the like. As the "substituent", halogen atom, alkyl group, hydroxyl group, alkoxy group, carboxyl group, alkoxycarbonyl group, amino group optionally having substituents, carbamoyl group optionally having substituents, acyl group, cyano group, nitro group, mercapto group, alkylthio group, aryl group, arylthio group, sulfo group, alkylsulfonyl group, arylsulfonyl group and the like can be mentioned. The detailed definition of each substituent is discussed later.

The term "cycloalkylalkyl group optionally having substituents" means a cycloalkylalkyl group optionally substituted by 1 to 5 substituents. Here, the term "cycloalkylalkyl group" means an alkyl group, as defined above, substituted by a cycloalkyl group, as defined above, which is specifically exemplified by cyclopropylmethyl group, cyclobutylmethyl group, cyclopentylmethyl group, cyclohexylmethyl group, cycloheptylmethyl group and the like. As the "substituent", halogen atom, alkyl group, hydroxyl group, alkoxy group, carboxyl group, alkoxycarbonyl group, amino group optionally having substituents, aminocarbonyl group, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "aryl group optionally having substituents" means an aryl group optionally substituted by 1 to 5 substituents. Here, the "aryl group" means a mono- to tricyclic aryl group having 6 to 14 carbon atoms, which is specifically exemplified by phenyl group, naphthyl group, anthryl group, phenanthryl group, biphenyl group and the like. As the "substituent", halogen atom, alkyl group, hydroxyl group, alkoxy group, alkylenedioxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "aralkyl group optionally having substituents" means an aralkyl group optionally substituted by 1 to 5 substituents. Here, the term "aralkyl group" is an alkyl group, as defined above, substituted by an aryl group, as defined above, wherein the alkyl group and the aryl group may be taken together to form a ring, which is specifically exemplified by benzyl group, diphenylmethyl group, trityl group, phenethyl group, 3-phenylpropyl group, 2-phenylpropyl group, 4-phenylbutyl group, biphenylmethyl group, naphthylmethyl group and the like, and as a case forming a ring, benzocyclobutenyl group, indanyl group and the like can be mentioned. As the "substituent", halogen atom, halogenated alkyl group, alkyl group, alkylene group, aryl group, aralkyl group, hydroxyl group, alkoxy group, aryloxy group, alkylenedioxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "heteroaryl group optionally having substituents" means a heteroaryl group optionally substituted by 1 to 5 substituents. Here, the term "heteroaryl group" means an aromatic heterocyclic group having 1 to 13 carbon atoms, which has 1 to 5 hetero atoms selected from oxygen atom, nitrogen atom and sulfur atom, and which optionally form a fused ring. Specifically, term "heteroaryl group" includes aromatic heterocyclic groups such as pyrrolyl group, furyl group, thienyl group, pyridyl group, pyrazolyl group, imidazolyl group, oxazolyl group, thiazolyl group, pyrazinyl group, pyridazinyl group, pyrimidinyl group, oxadiazolyl group, thiadiazolyl group, triazolyl group, triazinyl group, indolyl group, quinolyl group and the like. As the "substituent", halogen atom, alkyl group, hydroxyl group, alkoxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "heteroarylalkyl group optionally having substituents" means a heteroarylalkyl group optionally substituted by 1 to 5 substituents. Here, the "heteroarylalkyl group" is an alkyl group, as defined above, substituted by a heteroaryl group, as defined above, which is specifically exemplified by furylmethyl group, thienylmethyl group, pyrrolylmethyl group, oxazolylmethyl group, thiazolylmethyl group, imidazolylmethyl group, pyrazolylmethyl group, pyridylmethyl group, pyridazinylmethyl group, pyrimidinylmethyl group, pyrazinylmethyl group and the like. As the "substituent", halogen atom, alkyl group, hydroxyl group, alkoxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "heterocyclic group optionally having substituents" means a heterocyclic group optionally substituted by 1 to 5 substituents. Here, the "heterocyclic group" means a cycloalkyl group (as defined above; cyclic alkyl group having 3 to 7 carbon atoms) having at least one hetero atom (oxygen atom, nitrogen atom, sulfur atom etc.), which is specifically exemplified by pyrrolidinyl group, tetrahydrofuranyl group, tetrahydrothiophenyl group, piperidyl group, tetrahydropyranyl group, morpholinyl group, imidazolidinyl group, pyrazolidinyl group, piperazinyl group, quinuclidinyl group and the like. As the "substituent", halogen atom, alkyl group, hydroxyl group, alkoxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "heterocyclic-alkyl group optionally having substituents" means a heterocyclic-alkyl group optionally substituted by 1 to 5 substituents. Here, the "heterocyclic-alkyl group" means an alkyl group (as defined above) substituted by a heterocyclic group (as defined above), which is specifically exemplified by pyrrolidinylmethyl group, tetrahydrofuranylmethyl group, tetrahydrothiophenylmethyl group, piperidylmethyl group, pyranylmethyl group, morpholinylmethyl group, imidazolidinylmethyl group, pyrazolidinylmethyl group, piperazinylmethyl group, quinuclidinylmethyl group, piperidinomethyl group, morpholinomethyl group and the like. As the "substituent", halogen atom, alkyl group, hydroxyl group, alkoxy group, carboxyl group, alkoxycarbonyl group, amino group optionally having substituents, carbamoyl group optionally having substituents, acyl group, cyano group, nitro group, mercapto group, alkylthio group, arylthio group, sulfo group, alkylsulfonyl group, arylsulfonyl group and the like can be mentioned. The detailed definition of each substituent is discussed later.

The term "amino group optionally having substituents" means an amino group optionally substituted by 1 to 3 substituents. As the "substituent", alkyl group, cycloalkyl group, aryl group, aralkyl group, acyl group, alkoxycarbonyl group and the like can be mentioned. Two or more substituents may be linked to form a ring. The detailed definition of each substituent is discussed later.

The definition of each substituent is explained in the following.

The term "halogen atom" is a fluorine atom, a chlorine atom, a bromine atom or an iodine atom.

The term "alkyl group" is as defined above, and means a straight chain or branched chain alkyl group having 1 to 10 carbon atoms.

The term "alkoxy group" is a straight chain or branched chain alkoxy group having 1 to 6 carbon atoms, which is specifically exemplified by methoxy group, ethoxy group, n-propoxy group, isopropoxy group, n-butoxy group, isobutoxy group, sec-butoxy group, tert-butoxy group, n-pentyloxy group, isopentyloxy group, tert-pentyloxy group, n-hexyloxy group, 2-hexyloxy group and the like.

The term "alkoxycarbonyl group" means a straight chain or branched chain alkoxycarbonyl group having 2 to 5 carbon atoms, which is specifically exemplified by methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group and the like.

The term "amino group optionally having substituents" is as defined above.

The term "acyl group" is an acyl group having, as a constituent element, a hydrogen atom, a straight chain or branched chain alkyl group having 1 to 6 carbon atoms, a cycloalkyl group, an aryl group, an alkenyl group (a group having one or more double bonds at any position of alkyl group (as the alkyl group, the aforementioned "alkyl group" having 2 or more carbon atoms can be mentioned), which is specifically exemplified by vinyl group, propenyl group, butenyl group, pentenyl group and the like). As the straight chain or branched chain alkyl group having 1 to 6 carbon atoms, those mentioned above for the "alkyl group", which has not more than 6 carbon atoms can be mentioned. As the cycloalkyl group and aryl group, those respectively mentioned above can be mentioned. The alkyl moiety, cycloalkyl moiety and aryl moiety in the acyl group each may have a substituent, and as such substituent, those respectively mentioned above can be mentioned. As the acyl group, formyl group, acetyl group, propionyl group, butyloyl group, isobutyloyl group, valeroyl group, isovaleroyl group, pivaloyl group, hexanoyl group, acryloyl group, methacryloyl group, crotonoyl group, isocrotonoyl group, benzoyl group, naphthoyl group and the like can be specifically mentioned.

The term "carbamoyl group optionally having substituents" means a carbamoyl group optionally substituted by 1 to 5 substituents. As the "substituent", alkyl group (as defined above), cycloalkyl group (as defined above), aryl group (as defined above), aralkyl group (as defined above), acyl group (as defined above) and the like can be mentioned.

The term "alkylthio group" means a thio group substituted by a straight chain or branched chain alkyl group having 1 to 6 carbon atoms (as defined above), which is specifically exemplified by methylthio group, ethylthio group, propylthio group, isopropylthio group, n-butylthio group, isobutylthio group, sec-butylthio group, tert-butylthio group, n-pentylthio group, isopentylthio group, tert-pentylthio group, neopentylthio group, 2-pentylthio group, 3-pentylthio group, n-hexylthio group, 2-hexylthio group and the like.

The term "arylthio group" means a thio group substituted by an optionally substituted aryl group (as defined above), which is specifically exemplified by phenylthio group, naphthylthio group, anthrylthio group, phenanthrylthio group, biphenylthio group and the like.

The term "alkylsulfonyl group" means a sulfonyl group substituted by a straight chain or branched chain alkyl group having 1 to 6 carbon atoms (as defined above), which is specifically exemplified by methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, tert-pentylsulfonyl group, neopentylsulfonyl group, 2-pentylsulfonyl group, 3-pentylsulfonyl group, n-hexylsulfonyl group, 2-hexylsulfonyl group and the like.

The term "arylsulfonyl group" means a sulfonyl group substituted by an optionally substituted aryl group (as defined above), which is specifically exemplified by phenylsulfonyl group, toluenesulfonyl group, naphthylsulfonyl group, anthrylsulfonyl group, phenanthrylsulfonyl group, biphenylsulfonyl group and the like.

The term "alkylene group" means a straight chain or branched chain alkylene group having 1 to 8 carbon atoms, which is specifically exemplified by methylene group, ethylene group, trimethylene group, tetramethylene group, pentamethylene group, hexamethylene group, heptamethylene group, octamethylene group, propylene group, ethylethylene group, dimethylmethylene group, dimethyltrimethylene group and the like.

The term "alkylenedioxy group" means an alkylenedioxy group containing a straight chain or branched chain alkylene group having 1 to 8 carbon atoms (as defined above) as a constituent element, which is specifically exemplified by methylenedioxy group, ethylenedioxy group and the like.

The term "halogenated alkyl group" is an alkyl group (as defined above) substituted by 1 to 3 halogen atoms (as defined above), which is specifically exemplified by chloromethyl group, chloroethyl group, dichloromethyl group, dichloroethyl group, trichloromethyl group, trichloroethyl group, bromomethyl group, bromoethyl group, dibromomethyl group, dibromoethyl group, tribromomethyl group, tribromoethyl, fluoromethyl group, fluoroethyl group, difluoromethyl group, difluoroethyl group, trifluoromethyl group, trifluoroethyl group and the like, with preference given to a trihalomethyl group such as trichloromethyl group, tribromomethyl group, trifluoromethyl group and the like.

While the term "aryl group" is as defined above, preferred are phenyl group and benzyl group.

The term "aryloxy group" means an aryloxy group having an aryl group (as defined above) as a constituent element, which is specifically exemplified by phenoxy group, naphthyloxy group, anthryloxy group and the like, with preference given to phenoxy group.

In the term "amino group optionally having substituents", as the ring formed by two or more substituents bonded to each other, pyrrolidino group, piperidino group, piperazino group and the like can be mentioned.

In the formula (I), preferable examples of R include:
alkyl group optionally having substituent(s),
cycloalkylalkyl group optionally having substituent(s),
aryl group optionally having substituent(s),
aralkyl group optionally having substituent(s),
heteroarylalkyl group optionally having substituent(s),
A-B- wherein A is:
an alkyl group optionally having substituent(s) (as defined above),
cycloalkyl group optionally having substituent(s) (as defined above),
aryl group optionally having substituent(s) (as defined above),
heteroaryl group optionally having substituent(s) (as defined above),
heterocyclic group optionally having substituent(s), and
B is an oxygen atom or a sulfur atom; and
the formula (II)

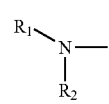

(II)

wherein $R_1$ and $R_2$ are the same or different and each is:
a hydrogen atom, an alkyl group optionally having substituent(s) (as defined above), a cycloalkyl group optionally having substituent(s) (as defined above), an aryl group optionally having substituent(s) (as defined above), a heteroaryl group optionally having substituent(s) (as defined above) or a heterocyclic group optionally having substituent(s) (as defined above).

As the A-B- in the formula (I), for example, 2,6-dichlorophenoxy group, 2-chloro-6-methoxyphenoxy group, 2-chloro-6-fluorophenoxy group, 2,6-dichlorothiophenoxy group, 2-chloro-6-methoxythiophenoxy group and 2-chloro-6-fluorothiophenoxy group can be mentioned, with preference given to 2-chloro-6-fluorophenoxy group and 2-chloro-6-fluorothiophenoxy group.

Preferable examples of the formula (II) include 2,6-dichloroanilino group, 2-chloro-6-methoxyanilino group and 2-chloro-6-fluoroanilino group, with particular preference given to 2-chloro-6-fluoroanilino group.

Particularly preferably, aralkyl group optionally having substituent(s), heteroarylalkyl group optionally having substituent(s), A-B- and the above-mentioned formula (II) can be mentioned as examples of formula (II).

As preferable examples of R of the formula (I), pentyl group, isopropyl group, tert-butyl group, cyclopropylmethyl group, cyclopentylmethyl group, cyclohexylmethyl group, 2,6-dichlorophenyl group, 2-chloro-6-methoxyphenyl group, 2-chloro-6-fluorophenyl group, 2-bromobenzyl group, 2-chlorobenzyl group, 4-trifluoromethylbenzyl group, 2,6-dichlorobenzyl group, 2-chloro-6-methoxybenzyl group, 2-chloro-6-fluorobenzyl group, 2-chloro-6-nitrobenzyl group, 2,6-difluorobenzyl group, 3,4-dichlorobenzyl group, 2,6-dichloro-3-nitrobenzyl group, furylmethyl group, thienylmethyl group, pyrrolylmethyl group, pyridylmethyl group, pyrimidinylmethyl group, 2,6-dichlorophenoxy group, 2-chloro-6-methoxyphenoxy group, 2-chloro-6-fluorophenoxy group, 2,6-dichlorothiophenoxy group, 2-chloro-6-methoxythiophenoxy group, 2-chloro-6-fluorothiophenoxy group, 2,6-dichloroanilino group, 2-chloro-6-methoxyanilino group and 2-chloro-6-fluoroanilino group can be mentioned, with particular preference given to 2-bromobenzyl group, 2-chlorobenzyl group, 4-trifluoromethylbenzyl group, 2,6-dichlorobenzyl group, 2-chloro-6-methoxybenzyl group, 2-chloro-6-fluorobenzyl group, 2-chloro-6-nitrobenzyl group, 2,6-difluorobenzyl group, 3,4-dichlorobenzyl group and 2,6-dichloro-3-nitrobenzyl group.

In the formula (I), X is an amino group optionally having substituent(s) (as defined above). Preferably, X is methylamino group, cyclopropylamino group, pyrrolidino group and amino group, and particularly preferably, amino group can be mentioned.

In the formula (I), as a preferable combination of $Y_1$ and $Y_2$, a case wherein both $Y_1$ and $Y_2$ are nitrogen atoms and a case wherein one of $Y_1$ and $Y_2$ is a nitrogen atom can be mentioned. A particularly preferable combination is a case wherein both $Y_1$ and $Y_2$ are nitrogen atoms.

The compound represented by the formula (I) also exists as various isomers. That is, the compound represented by the formula (I) may have one or more asymmetric centers, and encompasses all of pure optical isomer, partially purified optical isomer, racemic mixture, and pure diastereomer, partially purified diastereomer, a mixture of these and the like. In addition, the compound represented by the formula (I) includes structural isomers such as tautomer and the like and geometric isomer, which isomers are all encompassed in the present invention.

As the tautomer, for example, the following structures can be mentioned:

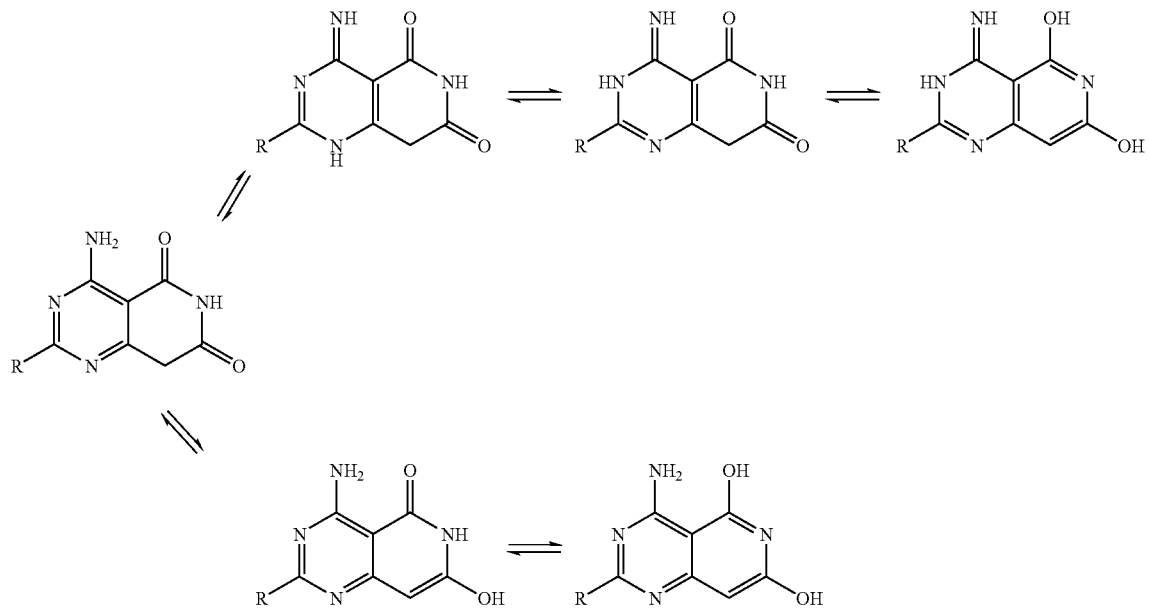

wherein R is as defined above.

The "pharmaceutically acceptable salt" may be any salt as long as it is a nontoxic salt together with a compound of the aforementioned formula (I) (including an isomer thereof). For example, salt with inorganic acid such as hydrofluoride, hydrochloride, hydrobromide, hydroiodide, sulfate, nitrate, phosphate, carbonate, hydrogencarbonate, perchlorate and the like; salt with organic acid such as formate, acetate, trifluoroacetate, propionate, oxalate, glycolate, succinate, lactate, maleate, hydroxymaleate, methylmaleate, fumarate, adipate, tartrate, malate, citrate, benzoate, cinnamate, ascorbate, salicylate, 2-acetoxybenzoate, nicotinate, isonicotinate and the like; salt with organic sulfonic acid such as methanesulfonate, ethanesulfonate, isethionate, benzenesulfonate, p-toluenesulfonate, naphthalenesulfonate, hydroxybenzenesulfonate, dihydroxybenzenesulfonate and the like; salt with acidic amino acid such as aspartate, glutamate and the like; alkali metal salt such as sodium salt, potassium salt and the like; alkaline earth metal salt such as magnesium salt, calcium salt and the like; ammonium salt; salt with organic base such as trimethylamine salt, triethylamine salt, pyridine salt, picoline salt, dicyclohexylamine salt, N,N'-dibenzylethylenediamine salt and the like; salt with basic amino acid such as lysine salt, arginine salt and the like; and the like can be mentioned. In some cases, the salt may be a solvate or hydrate with water, alcohol and the like.

The compound of the formula (I) of the present invention has a superior TNF-α production inhibitory action in mammals such as human, bovine, horse, dog, mouse, rat and the like. Therefore, it is expected to be a therapeutic agent for diseases, for which inhibition of the production of TNF-α is effective, such as septic shock, sepsis, endotoxic shock, hemodynamic shock, post ischemic reperfusion injury, meningitis, psoriasis, congestive cardiomyopathy, fibrosis, hepatitis, non-insulin dependent diabetes mellitus (NIDDM), graft rejection, graft versus host disease, cancer, cachexia, autoimmune diseases (systemic lupus erythematosus, rheumatic disease, allergy, multiple sclerosis, autoimmune uveitis, nephrotic syndrome, type I diabetes (IDDM) etc.), arthritis (rheumatoid arthritis, rheumatoid spondylitis, steoarthrosis, other arthritis), inflammatory bone diseases, bone absorption diseases, Behcet's syndrome, infectious diseases (opportunistic infectious disease in AIDS, cerebral malaria, mycobacterial infectious disease etc.), Crohn's disease, ulcerative colitis, ENL in leprosy, radiation damage, and damage of aircell by high oxygen, particularly, Crohn's disease, ulcerative colitis, sepsis, rheumatoid arthritis, autoimmune disease and the like. Even when merely referred to as a therapeutic agent in the present invention, the treatment encompasses any management such as prophylaxis, alleviation of symptoms, decrease of symptoms, inhibition of progression and the like.

The compound of the formula (I) of the present invention, an isomer or solvate thereof or a pharmaceutically acceptable salt thereof is admixed with a conventional pharmacologically acceptable carrier, an excipient, a diluent, an extender, a disintegrant, a stabilizer, a preservative, a buffer, an emulsifier, an aromatic, a coloring agent, a sweetener, a thickening agent, a corrigent, a dissolution aids, other additive and the like, which are known per se, and can be administered orally or parenterally in the form of a tablet, a pill, a powder, a granule, a suppository, an injection, an eye drop, a liquid, a capsule, a troche, an aerosol, an elixir, a suspension, an emulsion, a syrup and the like.

When a solid preparation is to be made, additives such as sucrose, lactose, cellulose sugar, D-mannitol, multitol, dextran, starches, agar, arginates, chitins, chitosans, pectins, tragacanth gums, gum arabics, gelatins, collagens, casein, albumin, calcium phosphate, sorbitol, glycine, carboxymethyl cellulose, polyvinylpyrrolidone, hydroxypropyl cellulose, hydroxypropylmethyl cellulose, glycerine, polyethylene glycol, sodium hydrogen carbonate, magnesium stearate, talc and the like are used. Moreover, tablets can be made to have a conventional film as necessary, such as sugar-coated tablet, enteric coated tablet, film-coated tablet, two-layer tablet or multi-layer tablet.

When a semi-solid preparation is to be produced, animal and plant fats and oils (olive oil, corn oil, castor oil etc.), mineral fats and oils (petrolatum, white petrolatum, solid paraffin etc.), waxes (jojoba oil, carnauba wax, bee wax etc.), partially synthesized or totally synthesized glycerine fatty acid (lauryl acid, myristic acid, palmitic acid etc.) ester and the like are used.

When a liquid preparation is to be produced, additives such as sodium chloride, glucose, sorbitol, glycerine, olive oil, propylene glycol, ethyl alcohol and the like can be mentioned. In particular, when an injection is to be produced, an aseptic aqueous solution, such as saline, an isotonic solution and an oily solution, such as sesame oil and soy bean oil are used. Where necessary, a suitable suspending agent, such as carboxymethyl cellulose sodium, a nonionic surfactant, a dissolution aids, such as benzyl benzoate, benzyl alcohol and the like may be used in combination. Moreover, when an eye drop is to be produced, an aqueous liquid or an aqueous solution can be mentioned. In particular, sterile aqueous solution for injection can be mentioned. The liquid for instillation may contain various additives such as a buffer, an isotonicity agent, a dissolution aids, a preservative, a thickening agent, a chelating agent, a pH adjuster and an aromatic.

The compound of the present invention can be also used as a pharmaceutical agent for animals, not to mention a pharmaceutical agent for human.

The dose is appropriately determined according to the kind and severity of disease, a compound to be administered, administration route, and age, sex, body weight and the like of patient (subject of administration).

The compound represented by the formula (I) of the present invention, an isomer or solvate thereof and a pharmaceutically acceptable salt thereof utilize the characteristics based on the kind of basic skeleton or substituent, and can be produced by various known synthetic methods. For example, they can be produced according to, but not limited to, the following synthetic methods, which can be appropriately modified on demand. As such modification, alkylation, acylation, amination, imination, halogenation, reduction, oxidization and the like can be mentioned, and conventional reaction or method used in the art are used. Depending on the kind of the functional group, it may be effective for the production technique to substitute the functional group with a suitable protecting group (group easily convertible to a functional group) in the stage of a starting material or an intermediate. As such functional group, for example, an amino group, a hydroxyl group, a carboxyl group and the like can be mentioned and as a protecting group therefore, for example, the protecting groups described in Greene and Wuts, *Protective Groups in Organic Synthesis,* 2nd ed. and the like can be mentioned, which may be appropriately selected and used according to reaction conditions. In such a method, a functional group is introduced, the reaction is carried out and the protecting group is eliminated as necessary to give a desired compound.

Synthetic method:

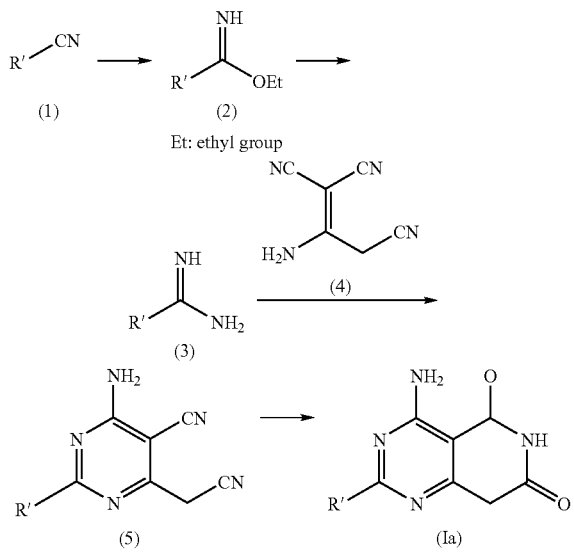

wherein R' is an alkyl group, a cycloalkyl group, a cycloalkylalkyl group, an aryl group, an aralkyl group, a heteroaryl group, a heteroarylalkyl group, a heterocyclic group or a heterocyclic-alkyl group, each of which optionally has substituent(s).

The corresponding nitrile compound (1) is converted to amidine compound (3) [carried out by, for example, Pinner method, a method described in The Chemical Society of Japan ed., *Jikken Kagaku Kouza* (4th edition), vol. 20 (1992)(MARUZEN) and the like], which is reacted with 2-amino-1,1,3-tricyano-1-propene (4) to form a pyrimidine ring (5). The reaction is carried out in an organic solvent inert to the reaction such as aromatic hydrocarbons (e.g., toluene and the like) by heating in the presence of an organic base (e.g., N,N-diisopropylethylamine). Finally, (5) is cyclized under acidic conditions to give the object compound (Ia). The reaction is carried out in a acidic solvent such as hydrochloric acid and the like (may be a mixed solvent with polar organic solvent such as 1,4-dioxane and the like) with heating.

(Ia: compound of the formula (I) wherein R is an alkyl group, a cycloalkyl group, a cycloalkylalkyl group, an aryl group, an aralkyl group, a heteroaryl group, a heteroarylalkyl group, a heterocyclic group or a heterocyclic-alkyl group, each optionally having substituent(s), $Y_1$ and $Y_2$ are both nitrogen atoms and X is an amino group).

Various compounds of the present invention and intermediates obtained by the above-mentioned production method can be converted to various compounds of the present invention and intermediates having an amino group having substituent(s) by further subjecting to a reaction such as alkylation, acylation, halogenation, nucleophilic substitution and the like. The alkylation and nucleophilic substitution reaction can be carried out by, for example, a method described in The Chemical Society of Japan ed., *Jikken Kagaku Kouza* (4th edition), vol. 20 (1992)(Maruzen) and the like, acylation can be carried out by, for example, a method described in, for example, The Chemical Society of Japan ed., *Jikken Kagaku Kouza* (4th edition), vol. 22 (1992)(Maruzen) and the like, and halogenation can be carried out by, for example, a method described in, for example, The Chemical Society of Japan ed., *Jikken Kagaku Kouza* (4th edition), vol. 19 (1992)(Maruzen) and the like.

In addition, the starting material compound (1) of the compound represented by the formula (I) of the present invention can be produced by, for example, a conventional method using a known reaction shown in the following synthetic scheme.

Synthesis from aromatic carboxylic acid, aldehyde:

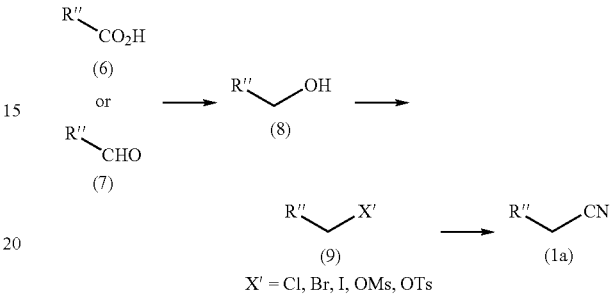

X' = Cl, Br, I, OMs, OTs wherein R" is a cycloalkyl group, an aryl group, a heteroaryl group or a heterocyclic group, each optionally having substituents.

The hydroxyl group of alcohol obtained by reducing the corresponding carboxylic acid and aldehyde, which can be performed by a method described in, for example, The Chemical Society of Japan ed., *Jikken Kagaku Kouza* (4th edition), vol. 26 (1992)(Maruzen) and the like, is converted to a leaving group (e.g., halogen atom, a methanesulfonyl group, a toluenesulfonyl group etc.), which can be performed by a method described in, for example, The Chemical Society of Japan ed., *Jikken Kagaku Kouza* (4th edition), vols. 19, 24 (1992)(Maruzen) and the like, which is then reacted with metallocyanide and the like, which can be performed by a method described in, for example, The Chemical Society of Japan ed., *Jikken Kagaku Kouza* (4th edition), vol. 20 (1992)(Maruzen) and the like, whereby compound (Ia) (starting material compound (1) wherein R' is a cycloalkylalkyl group, an aralkyl group, a heteroarylalkyl group or a heterocyclic-alkyl group, each optionally having substituents) is obtained.

Synthesis from toluene-type compound:

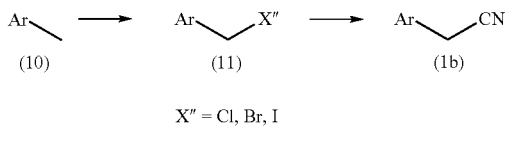

X" = Cl, Br, I wherein Ar is an aryl group optionally having substituents or a heteroaryl group optionally having substituents.

The benzyl position of the corresponding toluene-type compound is halogenated, which can be performed by a method described in, for example, The Chemical Society of Japan ed., *Jikken Kagaku Kouza* (4th edition), vol. 19 (1992)(Maruzen) and the like, and then reacted with a metallocyanide and the like, which can be performed by a method described in, for example, The Chemical Society of Japan ed., *Jikken Kagaku Kouza* (4th edition), vol. 20 (1992)(Maruzen) and the like, whereby compound (1b) (starting material compound (1) wherein R' is an aralkyl group optionally having substituent(s) or a heteroarylalkyl group optionally having substituent(s)) can be obtained.

EXAMPLES

The present invention is explained concretely and in detail in the following by referring to the Examples, which are not to be construed as limitative. The structure of the compound produced in each Example is shown in Table 1-Table 11 below. In addition, the production methods and the like of a part of the Examples are described in more detail.

Synthetic Example 1

Step 1

Benzyl cyanide (1 g, 8.5 mmol) was dissolved in 4N hydrochloric acid dioxane solution (10 ml) and ethanol (2 ml), and the mixture was stirred at room temperature for 2 days. The solvent was evaporated and the obtained crude product was dissolved in ethanol (10 ml). Ammonium carbonate (2 g) was added, and the mixture was stirred overnight. After filtration of ammonium carbonate, the solvent was evaporated to give a crude product. Toluene (5 ml), diisopropylethylamine (0.7 ml, 4 mmol) and 2-amino-1,1,3-tricyano-1-propene (264 mg, 2 mmol) were added to 442 mg of the obtained crude product, and the mixture was stirred overnight at 110° C. A treatment according to a conventional method using ethyl acetate as an extraction solvent gave a crude product, which was successively purified by silica gel column chromatography to give a nitrile intermediate.

Step 2

The nitrile intermediate (60 mg, 0.24 mmol) obtained in Step 1 was dissolved in concentrated hydrochloric acid (2 ml) and dioxane (2 ml), and after stirring at 80° C. for 2 hr, the solvent was evaporated and the obtained crystals were washed with water to give a compound of Example 1 (17 mg, 26%).

MS (ESI) m/z: 269(M+H)+; $^1$H-NMR (300 MHz, DMSO-$d_6$) δ 3.91 (2H, s), 5.38 (1H, s), 7.24-7.36 (6H, m), 8.84 (1H, s), 9.24 (1H, s), 11.29 (1H, s), 13.12 (1H, s).

Synthetic Example 11

Step 1

2-Methoxybenzyl cyanide (1 g, 6.8 mmol) was dissolved in 4N hydrochloric acid dioxane solution (10 ml) and ethanol (2 ml) and the mixture was stirred at room temperature for 2 days. The solvent was evaporated and the obtained crude product was dissolved in ethanol (10 ml). Ammonium carbonate (1.0 g) was added, and the mixture was stirred overnight. After filtration of ammonium carbonate, the solvent was evaporated and toluene (10 ml), diisopropylethylamine (1.2 ml, 7.3 mmol) and 2-amino-1,1,3-tricyano-1-propene (510 mg, 4.2 mmol) were added to the obtained crude product. The mixture was stirred at 110° C. for 2 hr. A treatment according to a conventional method using ethyl acetate as an extraction solvent gave a crude product, which was successively purified by silica gel column chromatography to give a nitrile intermediate (60 mg).

Step 2

A nitrile intermediate (60 mg, 0.21 mmol) obtained in Step 1 was dissolved in concentrated hydrochloric acid (2 ml) and dioxane (2 ml) and, after stirring at 80° C. for 2 hr, the solvent was evaporated and the obtained crystals were washed with water to give a compound of Example 4 (15 mg, 24%).

MS (ESI) m/z 299(M+H)+; $^1$H-NMR (300 MHz, DMSO-$d_6$) δ 3.80 (2H, s), 4.98 (1H, s), 6.91 (1H, dd), 6.98 (1H, dd), 7.19 (1H, dd), 7.24 (1H, dd), 8.41 (1H, s), 9.19 (1H, s), 10.46 (1H, s), 12.23 (1H, s).

Step 3

Dichloromethane (2 ml) and 1M boron tribromide dichloromethane solution (1 ml) were added to the compound (5 mg) obtained in Step 2, and the mixture was stirred overnight at room temperature. The solvent was evaporated and the obtained crude product was subjected to reversed phase high performance liquid chromatography using octadodecyl group chemical binding type silica gel as a filler, eluted with a mixed solution of water and acetonitrile, which contained trifluoroacetic acid in 0.1%(v/v), and the obtained object fraction was lyophilized to give a compound of Example 11.

MS (ESI) m/z: 285(M+H)+

Synthetic Example 22

Step 1

2-Nitrobenzyl cyanide (1 g, 6.2 mmol) was dissolved in 4N hydrochloric acid dioxane solution (10 ml) and ethanol (2 ml) and the mixture was stirred at room temperature for 2 days. The solvent was evaporated and the obtained crude product was dissolved in ethanol (10 ml). Ammonium carbonate (1.0 g) was added, and the mixture was stirred overnight. After filtration of ammonium carbonate, the solvent was evaporated. Toluene (10 ml), diisopropylethylamine (1.2 ml, 7.3 mmol) and 2-amino-1,1,3-tricyano-1-propene (510 mg, 4.2 mmol) were added to the obtained crude product and the mixture was stirred at 110° C. for 2 hr. A treatment according to a conventional method using ethyl acetate as an extraction solvent gave a crude product, which was successively purified by silica gel column chromatography to give a nitrile intermediate (70 mg).

Step 2

The nitrile intermediate (70 mg, 0.21 mmol) obtained in Step 1 was dissolved in concentrated hydrochloric acid (2 ml) and dioxane (2 ml) and, after stirring at 80° C. for 2 hr, the solvent was evaporated. The obtained crystals were washed with water to give a compound of Example 5 (21 mg, 32%).

MS (ESI) m/z 314(M+H)+; $^1$H-NMR (300 MHz, DMSO-$d_6$) δ 4.28 (2H, s), 4.94 (1H, s), 7.57 (2H, dd), 7.72 (1H, dd), 8.10 (1H, d), 8.21 (1H, s), 9.11 (1H, s), 10.40 (1H, s), 12.34 (1H, s)

Step 3

The compound (40 mg) obtained in Step 2 was dissolved in ethanol (10 ml) and palladium carbon (10 mg) was added. The mixture was stirred in the presence of hydrogen for 2 hr. The solvent was evaporated and the obtained crude product was treated in the same manner as in Example 11 to give a compound of Example 22.

MS (ESI) m/z: 284(M+H)+; $^1$H-NMR (300 MHz, DMSO-$d_6$) δ 3.77 (2H, s), 5.06 (1H, s), 6.78-7.17 (5H, m), 8.03 (1H, s), 8.58 (1H, s), 9.19 (1H, s), 10.78 (1H, s).

Synthetic Example 38

Step 1

2-Chloro-6-methoxytoluene (5 g, 32 mmol) was dissolved in benzene (100 ml) and N-bromosuccinimide (6.8 g, 38 mmol) and perbenzoic acid (5 mg) were added. The mixture was stirred overnight at 80° C. A treatment according to a conventional method using ethyl acetate as an extraction solvent gave a crude product. The obtained crude product was dissolved in dimethyl sulfoxide (100 ml), sodium cyanide (1.86 g, 38 mmol) was added, and the mixture was stirred overnight at room temperature. A treatment according to a conventional method using ethyl acetate as an extraction solvent gave a crude product, which was successively purified by silica gel column chromatography to give a nitrile intermediate (4.3 g, 23.8 mmol).

Step 2

In the same manner as in the method of Example 1 using the nitrile intermediate (4.3 g, 23.8 mmol) obtained in Step 1 as a starting material, a compound of Example 38 was obtained.

MS (ESI) m/z: 333(M+H)+; $^1$H-NMR (300 MHz, DMSO-$d_6$) δ 3.91 (2H, s), 5.38 (1H, s), 7.24-7.36 (6H, m), 8.84 (1H, s), 9.24 (1H, s), 11.29 (1H, s), 13.12 (1H, s).

Synthetic Example 43

Step 1

2-Chloro-4,5-methylenedioxybenzyl chloride (2.5 g, 12.1 mmol) was dissolved in dimethyl sulfoxide (10 ml), sodium cyanide (720 mg, 14.5 mmol) was added, and the mixture was stirred overnight at room temperature. A treatment according to a conventional method using ethyl acetate as an extraction solvent gave a crude product, which was successively purified by silica gel column chromatography to give a nitrile intermediate (2.0 g, 10.3 mmol).

$^1$H-NMR (300 MHz, CDCl$_3$) δ 3.73 (2H, s), 6.01 (2H, s), 6.88 (1H, s), 6.95 (1H, s).

Step 2

In the same manner as in the method of Example 1 using the nitrile intermediate (2.0 g, 10.3 mmol) obtained in Step 1 as a starting material, a compound of Example 43 was obtained.

MS (ESI) m/z: 347(M+H)+; $^1$H-NMR (300 MHz, DMSO-$d_6$) δ 4.03 (2H, s), 5.59 (1H, s), 6.06 (2H, s), 7.07 (2H, d), 8.98 (1H, s), 9.28 (1H, s), 11.72 (1H, s), 13.38 (1H, s).

Synthetic Example 53

Step 1

Acetonitrile (70 ml), potassium carbonate (1.7 g, 12.3 mmol) and methyl iodide (0.71 ml, 12.3 mmol) were added to 2-chloro-4-hydroxybenzaldehyde (1.5 g, 9.6 mmol), and the mixture was stirred overnight at 50° C. A treatment according to a conventional method using ethyl acetate as an extraction solvent gave a crude product. The obtained crude product was dissolved in ethanol (30 ml) and sodium borohydride (433 mg, 9.6 mmol) were added, and the mixture was stirred overnight at room temperature. A treatment according to a conventional method using ethyl acetate as an extraction solvent gave a crude product. The obtained crude product was dissolved in thionyl chloride (5 ml) and, after stirring at room temperature for 4 hr, treated according to a conventional method using ethyl acetate as an extraction solvent. The obtained crude product was dissolved in dimethyl sulfoxide (30 ml), sodium cyanide (470 mg, 9.6 mmol) was added, and the mixture was stirred overnight at room temperature. A treatment according to a conventional method using ethyl acetate as an extraction solvent gave a crude product, which was successively purified by silica gel column chromatography to give a nitrile intermediate (770 mg, 4.25 mmol).

$^1$H-NMR (300 MHz, CDCl$_3$) δ 3.76 (2H, s), 3.81 (3H, s), 6.84 (1H, dd), 6.96 (1H, d), 7.38 (1H, d).

Step 2

In the same manner as in the method of Example 1 using the nitrile intermediate (770 mg, 4.25 mmol) obtained in Step 1 as a starting material, a compound of Example 53 was obtained.

MS (ESI) m/z: 333(M+H)+

Synthetic Example 54

Step 1

2-Chloro-3,4-dimethoxybenzaldehyde (2.5 g, 12.4 mmol) was dissolved in ethanol (50 ml), sodium borohydride (930 mg, 25 mmol) was added, and the mixture was stirred overnight at room temperature. A treatment according to a conventional method using ethyl acetate as an extraction solvent gave a crude product. The obtained crude product was dissolved in thionyl chloride (5 ml) and, after stirring at room temperature for 4 hr, treated according to a conventional method using ethyl acetate as an extraction solvent. The obtained crude product was dissolved in dimethyl sulfoxide (30 ml), sodium cyanide (610 mg, 12.4 mmol) was added, and the mixture was stirred overnight at room temperature. A treatment according to a conventional method using ethyl acetate as an extraction solvent gave a crude product, which was successively purified by silica gel column chromatography to give a nitrile intermediate (830 mg, 3.93 mmol).

Step 2

In the same manner as in the method of Example 1 using the nitrile intermediate (830 mg, 3.93 mmol) obtained in Step 1 as a starting material, a compound of Example 54 was obtained.

MS (ESI) m/z: 363(M+H)+; $^1$H-NMR (300 MHz, DMSO-$d_6$) δ 3.68 (3H, s), 3.77 (1H, s), 3.96 (2H, s), 5.01 (1H, s), 7.01 (1H, d), 7.11 (1H, s), 8.41 (1H, s), 9.16 (1H, s), 10.51 (1H, s), 12.38 (1H, s).

Synthetic Example 55

Step 1

2-Chloro-3-methylbenzoic acid (2.5 g, 14.5 mmol) was dissolved in tetrahydrofuran (100 ml), triethylamine (2.6 ml, 19 mmol) and ethyl chloroformate (1.7 ml, 17.5 mmol) were added under ice-cooling, and the mixture was stirred for 30 min. Three pieces of ice were added, sodium borohydride (1.2 g, 29 mmol) was added, and the mixture was stirred overnight at room temperature. A treatment according to a conventional method using ethyl acetate as an extraction solvent gave a crude product. The obtained crude product was dissolved in thionyl chloride (5 ml) and, after stirring at room temperature for 4 hr, treated according to a conventional method using ethyl acetate as an extraction solvent. The obtained crude product was dissolved in dimethyl sulfoxide (30 ml), sodium cyanide (720 mg, 14.5 mmol) was added, and the mixture was stirred overnight at room temperature. A treatment according to a conventional method using ethyl acetate as an extraction solvent gave a crude product, which was successively purified by silica gel column chromatography to give a nitrile intermediate (1.1 g, 6.67 mmol).

$^1$H-NMR (300 MHz, CDCl$_3$) δ 2.42 (3H, s), 3.83 (2H, s), 7.06-7.38(3H, m).

Step 2

In the same manner as in the method of Example 1 using the nitrile intermediate (1.1 g, 6.67 mmol) obtained in Step 1 as a starting material, a compound of Example 55 was obtained.

MS (ESI) m/z: 317(M+H)+; $^1$H-NMR (300 MHz, DMSO-d$_6$) δ 2.34 (3H, s), 4.10 (1H, s), 5.38 (1H, s), 7.20-7.39 (3H, m), 8.73 (1H, s), 9.25 (1H, s), 11.17 (1H, s), 12.91 (1H, s)

Synthetic Example 74

Step 1

2-Chlorobenzaldehyde (1.4 g, 10 mmol) was dissolved in tetrahydrofuran (50 ml), sodium hydride (416 mg, 10.4 mmol) was added, and the mixture was stirred at room temperature for 30 min. Cyanomethylphosphonoethyl (1.8 g, 10.2 mmol) was added, and the mixture was stirred overnight at 50° C. A treatment according to a conventional method using ethyl acetate as an extraction solvent gave a crude product. The obtained crude product was dissolved in ethyl acetate (20 ml), palladium carbon (100 mg) was added, and the mixture was stirred in the presence of hydrogen at room temperature for 5 hr. Celite filtration gave a nitrile intermediate.

$^1$H-NMR (300 MHz, CDCl$_3$) δ 2.68 (2H, dd), 3.09 (2H, dd), 7.20-7.41 (4H, m).

Step 2

In the same manner as in the method of Example 1 using the nitrile intermediate obtained in Step 1 as a starting material, a compound of Example 74 was obtained.

MS (ESI) m/z: 317(M+H)+

Synthetic Example 77

Step 1

2-Chloro-6-hydroxytoluene (1.38 g, 7.9 mmol) was dissolved in dimethylformamide (70 ml), ethyl iodide (0.93 ml, 11 mmol) and potassium carbonate (1.74 g, 12.6 mmol) were added, and the mixture was stirred overnight. A treatment according to a conventional method using ethyl acetate as an extraction solvent gave a crude product, which was dissolved in benzene (100 ml). N-Bromosuccinimide (1.9 g, 10.7 mmol) and perbenzoic acid (5 mg) were added, and the mixture was stirred overnight at 80° C. A treatment according to a conventional method using ethyl acetate as an extraction solvent gave a crude product. The obtained crude product was dissolved in dimethyl sulfoxide (10 ml), sodium cyanide (250 mg, 5 mmol) was added, and the mixture was stirred overnight at room temperature. A treatment according to a conventional method using ethyl acetate as an extraction solvent gave a crude product, which was successively purified by silica gel column chromatography to give a nitrile intermediate (0.8 g, 4.1 mmol).

Step 2

In the same manner as in the method of Example 1 using the nitrile intermediate (0.8 g, 4.1 mmol) obtained in Step 1 as a starting material, a compound of Example 77 was obtained.

MS (ESI) m/z: 347(M+H)+

Synthetic Example 80

Step 1

2,6-Dichloro-3-nitrobenzoic acid (5.0 g, 21.3 mmol) was dissolved in tetrahydrofuran (100 ml), 1M boranetetrahydrofuran (84 ml) was added under ice-cooling, and the mixture was heated under reflux for 2 days. A treatment according to a conventional method using ethyl acetate as an extraction solvent gave a crude product, which was dissolved in ethyl acetate (100 ml). Palladium carbon (400 mg) was added, and the mixture was stirred in the presence of hydrogen at room temperature for 6 hr. After celite filtration, the solvent was evaporated, which was successively purified by silica gel column chromatography to give aniline derivative (1.4 g, 7.3 mmol).

$^1$H-NMR (300 MHz, CDCl$_3$) δ 4.14 (2H, br), 4.95 (2H, s), 6.80 (1H, d), 7.16 (1H, d).

Step 2

The aniline derivative (1.4 g, 7.3 mmol) obtained in Step 1 was dissolved in dimethylformamide (50 ml), methyl iodide (1.4 ml, 22 mmol) and potassium carbonate (3.0 g, 22 mmol) were added, and the mixture was stirred overnight. A treatment according to a conventional method using ethyl acetate as an extraction solvent gave a crude product, which was successively purified by silica gel column chromatography to give a dimethylaniline derivative (1.1 g, 5.0 mmol).

$^1$H-NMR (300 MHz, CDCl$_3$) δ 2.80 (6H, s), 4.96 (2H, d), 7.01 (1H, d), 7.25 (1H, d).

Step 3

The dimethylaniline derivative (1.1 g, 5.0 mmol) obtained in Step 2 was dissolved in thionyl chloride (5 ml) and the mixture was stirred at room temperature for 2 hr. A treatment according to a conventional method using ethyl acetate as an extraction solvent gave a crude product, which was dissolved in dimethyl sulfoxide (20 ml). Sodium cyanide (245 mg, 5 mmol) was added, and the mixture was stirred overnight at room temperature. A treatment according to a conventional method using ethyl acetate as an extraction solvent gave a crude product, which was successively purified by silica gel column chromatography to give a nitrile intermediate (1 g, 4.4 mmol).

Step 4

In the same manner as in the method of Example 1 using the nitrile intermediate (1 g, 4.4 mmol) obtained in Step 3 as a starting material, a compound of Example 80 was obtained.

MS (ESI) m/z: 380(M+H)+; $^1$H-NMR (300 MHz, DMSO-d$_6$) δ 2.69 (6H, s), 4.22 (2H, s), 5.01 (1H, s), 7.15 (1H, d), 7.40 (1H, d), 8.40 (1H, s), 9.17 (1H, s), 10.57 (1H, s), 12.50 (1H, s).

Synthetic Example 84

Step 1

2-Chloro-3-methyl-6-fluorobenzyl alcohol (2.0 g, 13.2 mmol) was dissolved in thionyl chloride (5 ml) and the mixture was stirred at room temperature for 4 hrs. A treatment according to a conventional method using ethyl acetate as an extraction solvent gave a crude product, which was successively purified by silica gel column chromatography to give a benzyl chloride derivative (1.4 g, 7.3 mmol).

$^1$H-NMR (300 MHz, CDCl$_3$) δ 2.24 (3H, s), 4.78 (2H, s), 7.13 (2H, s).

Step 2

The benzyl chloride derivative (1.4 g, 7.3 mmol) obtained in Step 1 was dissolved in dimethyl sulfoxide (20 ml), potassium cyanide (568 mg, 8.75 mmol) was added, and the mixture was stirred overnight at room temperature. A treatment according to a conventional method using ethyl acetate as an extraction solvent gave a crude product, which was successively purified by silica gel column chromatography to give a nitrile intermediate (0.9 g, 4.9 mmol).

$^1$H-NMR (300 MHz, CDCl$_3$) δ 2.24 (3H, s), 3.83 (2H, s), 7.17 (2H, s).

Step 3

In the same manner as in the method of Example 1 using the nitrile intermediate (0.9 g, 4.9 mmol) obtained in Step 2 as a starting material, a compound of Example 84 was obtained.

MS (ESI) m/z: 335(M+H)+; $^1$H-NMR (300 MHz, DMSO-d$_6$) δ 2.21 (3H, s), 4.17 (2H, s), 5.64 (1H, s), 7.21-7.36 (2H, m), 8.97 (1H, s), 9.28 (1H, s), 11.77 (1H, s), 13.63 (1H, s).

In the following, in the same manner as in the methods described in the above-mentioned Examples, the Example compounds shown in Table 1-Table 11 were produced using the corresponding starting materials.

In the Tables, the following abbreviations are used. Ex: Example No., Syn: production method (number indicates Example No. wherein similar production was performed), Dat: physicochemical data, Me: methyl group, Ph: phenyl group.

TABLE 1

| Ex | Syn | R | Dat |
|---|---|---|---|
| 1 | — | benzyl | MS(ESI) m/z: $_{269}$(M+H)+; 1H-NMR(300 MHz, DMSO-d6) δ 3.91(2H, s), 5.38(1H, s), 7.24-7.36(6H, m), 8.84(1H, s), 9.24(1H, s), 11.29(1H, s), 13.12(1H, s). |
| 2 | 1 | 2-Br-benzyl | MS(ESI) m/z: $_{348}$(M+H)+; 1H-NMR(300 MHz, DMSO-d6) δ 4.04(2H, s), 5.08(1H, s), 7.21-7.26(1H, m), 7.33-7.41(2H, m), 7.61(1H, d), 8.51(1H, s), 9.18(1H, s), 10.73(1H, s), 12.60 (1H, s). |
| 3 | 1 | 2,6-diCl-benzyl | MS(ESI) m/z: $_{303}$(M+H)+; 1H-NMR(300 MHz, DMSO-d6) δ 4.21(2H, s), 4.98(1H, s), 7.31-7.49(1H, m), 7.50-7.58(2H, m), 8.32(1H, s), 9.15(1H, s), 10.46(1H, s), 12.48(1H, s). |
| 4 | 1 | 2-OMe-benzyl | MS(ESI) m/z: $_{299}$(M+H)+; 1H-NMR(300 MHz, DMSO-d6) δ 3.80(2H, s), 4.98(1H, s), 6.91(1H, dd), 6.98(1H, dd), 7.19 (1H, dd), 7.24(1H, dd), 8.41(1H, s), 9.19(1H, s), 10.46(1H, s), 12.23(1H, s). |
| 5 | 1 | 2-NO2-benzyl | MS(ESI) m/z: $_{314}$(M+H)+; 1H-NMR(300 MHz, DMSO-d6) δ 4.28(2H, s), 4.94(1H, s), 7.57(2H, dd), 7.72(1H, dd), 8.10 (1H, d), 8.21(1H, s), 9.11(1H, s), 10.40(1H, s), 12.34(1H, s). |
| 6 | 1 | CH(Ph)-phenyl | MS(ESI) m/z: $_{345}$(M+H)+; 1H-NMR(300 MHz, DMSO-d6) δ 5.36(1H, s), 5.48(1H, s), 7.21-7.43(10B, m), 8.90(1H, s), 9.29(1H, s), 11.32(1H, s), 13.21(1H, s). |

TABLE 1-continued

[Structure: 4-amino-pyrimidine fused pyridinone with R substituent at 2-position]

| Ex | Syn | R | Dat |
|---|---|---|---|
| 7 | 1 | 3-bromobenzyl | MS(ESI) m/z: 348(M+H)+; 1H-NMR(300 MHz, DMSO-d6) δ 3.90(2H, s), 5.28(1H, s), 7.24-7.36(5H, m), 8.68(1H, s), 9.22(1H, s), 10.98(1H, s), 12.78(1H, s). |

TABLE 2

| Ex | Syn | R | Dat |
|---|---|---|---|
| 8 | 1 | 1-phenylethyl (Me) | MS(ESI) m/z: 283(M+H)+; 1H-NMR(300 MHz, DMSO-d6) δ 4.18-4.23(1H, m), 5.68(1H, s), 7.20-7.43(5H, m), 9.15(1H, s), 9.35(1H, s), 11.82(1H, s), 13.43(1H, s). |
| 9 | 1 | 2-naphthylmethyl | MS(ESI) m/z: 319(M+H)+; 1H-NMR(300 MHz, DMSO-d6) δ 4.06(2H, s), 5.21(1H, s), 7.45-7.57(3H, m), 7.81-7.91(4H, m), 8.65(1H, s), 9.21(1H, s), 10.92(1H, s), 12.82(1H, s). |
| 10 | 1 | 2-(trifluoromethyl)benzyl | MS(ESI) m/z: 337(M+H)+; 1H-NMR(300 MHz, DMSO-d6) δ 4.17(2H, s), 5.33(1H, s), 7.49(2H, dd), 7.64(1H, dd), 7.73(1H, dd), 8.65(1H, s), 9.23(1H, s), 11.20(1H, s), 13.03(1H, s). |
| 11 | 1 | 2-hydroxybenzyl | MS(ESI) m/z: 285(M+H)+ |
| 12 | 1 | 2-chlorobenzyl | MS(ESI) m/z: 303(M+H)+; 1H-NMR(300 MHz, DMSO-d6) δ 4.01(2H, s), 4.94(1H, s), 7.24-7.50(4H, m), 8.37(1H, s), 9.18(1H, s), 10.39(1H, s), 12.36(1H, s). |
| 13 | 1 | 2-methylbenzyl | MS(ESI) m/z: 283(M+H)+; 1H-NMR(300 MHz, DMSO-d6) δ 2.30(3H, s), 3.94(2H, s), 5.40(1H, s), 7.11-7.28(5H, m), 8.78(1H, s), 9.23(1H, s), 11.29(1H, s), 13.12(1H, s). |
| 14 | 1 | 2-phenylethyl | MS(ESI) m/z: 283(M+H)+; 1H-NMR(300 MHz, DMSO-d6) δ 2.79-3.06(4H, m), 5.28(1H, s), 7.16-7.34(5H, m), 8.79(1H, s), 9.24(1H, s), 11.16(1H, s), 12.78(1H, s). |
| 15 | 1 | 3-phenylpropyl | MS(ESI) m/z: 297(M+H)+; 1H-NMR(300 MHz, DMSO-d6) δ 1.93-2.04(2H, m), 2.52-2.74(4H, m), 5.28(1H, s), 7.13-7.32(5H, m), 8.77(1H, s), 9.22(1H, s), 11.21(1H, s), 12.62(1H, s). |

TABLE 2-continued

| 16 | 1 | 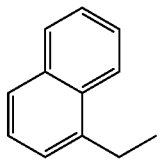 | MS(ESI) m/z: 319(M+H)+; 1H-NMR(300 MHz, DMSO-d6) δ 4.40(2H, s), 5.28(1H, s), 7.41-7.58(4H, m), 7.79-8.13(3H, m), 8.61(1H, s), 9.19(1H, s), 11.01(1H, s), 12.83(1H, s). |

TABLE 3

| 17 | 1 | 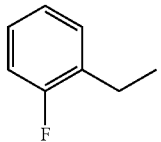 | MS(ESI) m/z: 287(M+H)+; 1H-NMR(300 MHz, DMSO-d6) δ 4.02(2H, s), 5.47(1H, s), 7.11-7.44(6H, m), 8.88(1H, s), 9.25(1H, s), 11.46(1H, s), 13.24(1H, s). |
| 18 | 1 | 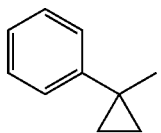 | MS(ESI) m/z: 295(M+H)+; 1H-NMR(300 MHz, DMSO-d6) δ 2.18-2.37(1H, m), 2.60-2.77(1H, m), 3.83-4.01(1H, m), 4.05-4.21(1H, m), 5.15(1H, s), 7.24-7.39(5H, m), 8.68(1H, s), 9.89(1H, s), 11.08(1H, s). |
| 19 | 1 | 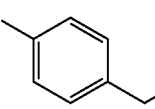 | MS(ESI) m/z: 348(M+H)+; 1H-NMR(300 MHz, DMSO-d6) δ 3.88(2H, s), 5.24(1H, s), 7.30(2H, d), 7.52(2H, d), 8.70(1H, s), 9.22(1H, s), 11.04(1H, s), 12.90(1H, s). |
| 20 | 1 | 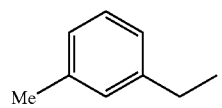 | MS(ESI) m/z: 283(M+H)+; 1H-NMR(300 MHz, DMSO-d6) δ 2.27(3H, s), 3.85(2H, s), 5.31(1H, s), 7.04-7.23(4H, m), 8.77(1H, s), 9.23(1H, s), 11.18(1H, s), 12.91(1H, s). |
| 21 | 1 | 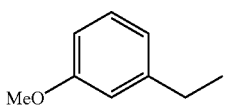 | MS(ESI) m/z: 299(M+H)+; 1H-NMR(300 MHz, DMSO-d6) δ 3.73(3H, s), 3.82(2H, s), 5.10(1H, s), 6.80-6.95(3H, m), 7.24(1H, dd), 8.59(1H, s), 9.20(1H, s), 10.77(1H, s), 12.57(1H, s). |
| 22 | — | 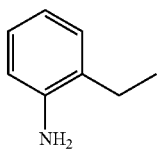 | MS(ESI) m/z: 284(M+H)+; 1H-NMR(300 MHz, DMSO-d6) δ 3.77(2H, s), 5.06(1H, s), 6.78-7.17(5H, m), 8.03(1H, s), 8.58(1H, s), 9.19(1H, s), 10.78(1H, s). |
| 23 | 1 | 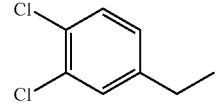 | MS(ESI) m/z: 338(M+H)+; 1H-NMR(300 MHz, DMSO-d6) δ 4.20(2H, s), 4.91(1H, s), 7.31-7.52(3H, m), 8.25(1H, s), 9.14(1H, s), 10.29(1H, s), 12.36(1H, s). |
| 24 | 1 | 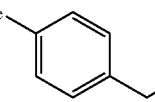 | MS(ESI) m/z: 283(M+H)+ |
| 25 | 1 | 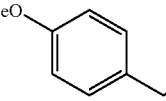 | MS(ESI) m/z: 299(M+H)+; 1H-NMR(300 MHz, DMSO-d6) δ 3.73(3H, s), 3.76(2H, s), 4.95(1H, s), 6.91(2H, d), 7.25(2H, d), 8.41(1H, s), 9.16(1H, s), 10.36(1H, s), 12.29(1H, s). |

TABLE 4

| # | | Structure | Data |
|---|---|---|---|
| 26 | 11 | 3-hydroxybenzyl | MS(ESI) m/z: 285(M+H)+; 1H-NMR(300 MHz, DMSO-d6) δ 3.71(2H, s), 4.93(1H, s), 6.60-6.74(3H, m), 7.11(1H, dd), 8.43(1H, s), 9.15(1H, s), 10.40(1H, s), 12.22(1H, s). |
| 27 | 11 | 4-hydroxybenzyl | MS(ESI) m/z: 285(M+H)+; 1H-NMR(300 MHz, DMSO-d6) δ 3.70(2H, s), 5.05(1H, s), 6.70(2H, d), 7.10(2H, d), 8.58(1H, s), 9.20(1H, s), 10.74(1H, s), 12.38(1H, s). |
| 28 | 1 | 4-chlorobenzyl | MS(ESI) m/z: 303(M+H)+; 1H-NMR(300 MHz, DMSO-d6) δ 3.87(2H, s), 5.04(1H, s), 7.3 14-7.46(4H, m), 8.52(1H, s), 9.19(1H, s), 10.62(1H, s), 12.50(1H, s). |
| 29 | 1 | 2,4-dichlorobenzyl | MS(ESI) m/z: 338(M+H)+; 1H-NMR(300 MHz, DMSO-d6) δ 4.20(2H, s), 5.61(1H, s), 7.43-7.67(3H, m), 8.95(1H, s), 9.30(1H, s), 11.719(1H, s), 13.55(1H, s). |
| 30 | 1 | 3-chlorobenzyl | MS(ESI) m/z: 303(M+H)+; 1H-NMR(300 MHz, DMSO-d6) δ 3.98(2H, s), 5.46(1H, s), 7.31-7.49(4H, m), 8.92(1H, s), 9.28(1H, s), 11.44(1H, s). |
| 31 | 1 | thiophen-3-ylmethyl | MS(ESI) m/z: 275(M+H)+; 1H-NMR(300 MHz, DMSO-d6) δ 3.93(2H, s), 5.43(1H, s), 7.09(1H, d), 7.39(1H, s), 7.51(1H, d), 8.91(1H, s), 9.26(1H, s), 11.41(1H, s). |
| 32 | 1 | 2,4,6-trimethylbenzyl | MS(ESI) m/z: 313(M+H); 1H-NMR(300 MHz, DMSO-d6) δ 2.20(3H, s), 2.22(6H, s), 3.92(2H, s), 5.11(1H, s), 6.82(2H, s), 8.37(1H, s), 9.18(1H, s)m 10.60(1H, s), 12.52(1H, s). |
| 33 | 1 | naphthalen-2-ylmethyl | MS(ESI) m/z: 307(M+H); 1H-NMR(300 MHz, DMSO-d6) δ 5.23(1H, s), 7.64-7.72(2H, m), 8.03-8.17(4H, m), 8.58(1H, s), 8.71(1H, s), 9.30(1H, s), 10.42(1H, s), 12.30(1H, s). |
| 34 | 1 | 3-methylbenzyl | MS(ESI) m/z: 271(M+H); 1H-NMR(300 MHz, DMSO-d6) δ 2.41(3H, s), 5.27(1H, s), 7.48-7.53(2H, m), 7.84-7.90(2H, m), 8.57(1H, s), 9.25(1H, s), 10.53(1H, s), 12. 18(1H, s). |

TABLE 5

| # | | Structure | Data |
|---|---|---|---|
| 35 | 1 | 4-methylbenzyl | MS(ESI) m/z: 271(M+H); 1H-NMR(300 MHz, DMSO-d6) δ 2.42(3H, s), 5.80(1H, s), 7.43(2H, d, J=10.2 Hz), 8.18(2H, d, J=10.2 Hz), 9.02(1H, s), 9.30(1H, s), 11.60(1H, s), 12.80(1H, s). |
| 36 | 1 | 2-iodobenzyl | MS(ESI) m/z: 395(M+H)+; 1H-NMR(300 MHz, DMSO-d6) δ 4.08(2H, s), 5.26(1H, s), 7.02-7.08(1H, m), 7.35-7.42(2H, m), 7.86-7.89(1H, m), 8.65(1H, brs), 9.24(1H, brs), 11.04(1H, brs), 12.89(1H, brs). |
| 37 | 1 | 2,3,4-trichlorobenzyl | MS(ESI) m/z: 371(M+H)+; 1H-NMR(300 MHz, DMSO-d6) δ 4.47(2H, s), 5.89(1H, s), 7.59(1H, d, J=8.7 Hz), 7.69(1H, d, J=9.0 Hz), 9.16(1H, brs), 9.35(1H, brs), 12.18(1H, brs). |

TABLE 5-continued

| # | n | R (structure) | Data |
|---|---|---|---|
| 38 | — | 2-OMe, 6-Cl benzyl (ethyl linker) | MS(ESI) m/z: 333(M+H)+; 1H-NMR(300 MHz, DMSO-d6) δ 3.91(2H, s), 5.38(1H, s), 7.24-7.36(6H, m), 8.84(1H, s), 9.24(1H, s), 11.29(1H, s), 13.12(1H, s). |
| 39 | 1 | 3-MeO benzyl | MS(ESI) m/z: 285(M+H); 1H-NMR(300 MHz, DMSO-d6) δ 3.82(3H, s), 5.19(1H, s), 7.22(1H, d, J=10.5 Hz), 7.52(1H, t, J=10.5 Hz), 7.58-7.64(2H,m), 8.47(1H, s), 9.23(1H, s), 10.37(1H, s), 12.03(1H, s). |
| 40 | 1 | 3,5-diMe benzyl | MS(ESI) m/z: 297(M+H); 1H-NMR(300 MHz, DMSO-d6) δ 2.23(6H, s), 3.73(2H, s), 4.93(1H, s), 6.80-6.94(3H, m), 8.37(1H, s), 9.18(1H, s), 10.27(1H, s), 12.21(1H, s). |
| 41 | 1 | n-pentyl | MS(ESI) m/z: 249(M+H); 1H-NMR(300 MHz, DMSO-d6) δ 0.83(3H, t, J=7.2 Hz), 1.27-1.36(4H, m), 1.65-1.77(2H, m), 2.63(2H, q, J=6.7 Hz), 5.78(1H, s), 9.12(1H, s), 9.32(1H, s), 11.95(1H, s), 13.46(1H, s). |
| 42 | 1 | 2-OH, 6-Cl benzyl | MS(ESI) m/z: 319(M+H)+; 1H-NMR(300 MHz, DMSO-d6) δ 4.01(2H, s), 5.22(1H, s), 6.78(1H, d), 6.908(1H, d), 7.12(1H, dd), 8.70(1H, s), 9.21(1H, s), 10.14(1H, s), 11.14(1H, s), 12.63(1H, s). |
| 43 | — | 4-Cl-benzo[1,3]dioxol-5-ylmethyl (ethyl linker) | MS(ESI) m/z: 347(M+H)+; 1H-NMR(300 MHz, DMSO-d6) δ 4.03(2H, s), 5.59(1H, s), 6.06(2H, s), 7.07(2H, d), 8.98(1H, s), 9.28(1H, s), 11.72(1H, s), 13.38(1H, s). |

TABLE 6

| # | n | R (structure) | Data |
|---|---|---|---|
| 45 | 1 | benzo[1,3]dioxol-5-ylmethyl | MS(ESI) m/z: 313(M+H); 1H-NMR(300 MHz, DMSO-d6) δ 3.66(2H, s), 5.98(2H, s), 6.80-6.98(3H, m), 8.40(1H, s), 9.18(1H, s), 10.38(1H, s), 12.22(1H, s). |
| 46 | 1 | 4-benzyl benzyl | MS(ESI) m/z: 359(M+H); 1H-NMR(300 MHz, DMSO-d6) δ 3.80(2H, s), 3.90(2H, s), 4.97(1H, s), 7.10-7.30(9H, m), 8.42(1H, s), 9.17(1H, s), 10.49(1H, s), 12.38(1H, s). |
| 47 | 1 | 2-phenyl benzyl | MS(ESI) m/z: 345(M+H); 1H-NMR(300 MHz, DMSO-d6) δ 3.84(2H, s), 4.99(1H, s), 7.20-7.42(9H, m), 8.48(1H, s), 9.16(1H, s), 10.67(1H, s), 12.37(1H, s). |
| 48 | 1 | 4-Br phenyl | MS(ESI) m/z: 333,335(M+H); 1H-NMR(300 MHz, DMSO-d6) δ 5.27(1H, s), 7.83(2H, d, J=10.5 Hz), 8.07(2H, d, J=10.5 Hz), 8.60(1H, s), 9.28(1H, s), 10.61(1H, s), 12.33(1H, s). |
| 49 | 1 | 3-Cl phenyl | MS(ESI) m/z: 289,291(M+H); 1H-NMR(300 MHz, DMSO-d6) δ 5.32(1H, s), 7.62(1H, t, J=10.2 Hz), 7.77(1H, d, J=10.2 Hz), 8.06(1H, d, J=10.2 Hz), 8.17(1H, s), 8.63(1H, s), 9.26(1H, s), 10.63(1H, s), 12.37(1H, s). |

TABLE 6-continued

| 50 | 1 | 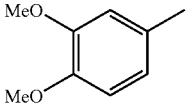 | MS(ESI) m/z: 315(M+H); 1H-NMR(300 MHz, DMSO-d6) δ 3.82(3H, s), 3.84(3H, s), 5.22(1H, s), 7.17(1H, d, J=10.5 Hz), 7.67(1H, s), 7.77(1H, d, J=10.5 Hz), 8.43(1H, s), 9.24(1H, s), 10.41(1H, s), 11.97(1H, s). |
|---|---|---|---|
| 51 | 1 | 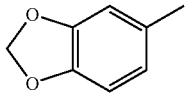 | MS(ESI) m/z: 299(M+H); 1H-NMR(300 MHz, DMSO-d6) δ 5.42(1H, s), 6.18(2H, s), 7.17(1H, d, J=10.5 Hz), 7.80 81H, s), 8.87(1H, d, J=10.5 Hz), 9.17(1H, s), 9.39(1H, s), 12.00(1H, s), 13.10(1H, s). |
| 53 | — | 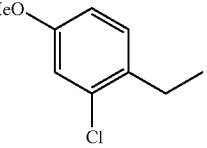 | MS(ESI) m/z: 333(M+H)+ |
| 54 | — | 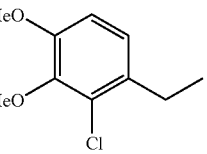 | MS(ESI) m/z: 363(M+H)+; 1H-NMR(300 MHz, DMSO-d6) δ 3.68(3H, s), 3.77(1H, s), 3.96(2H, s), 5.01(1H, s), 7.01(1H, d), 7.11(1H, s), 8.41(1H, s), 9.16(1H, s), 10.51(1H, s), 12.38 (1H,s). |

TABLE 7

| 55 | — | 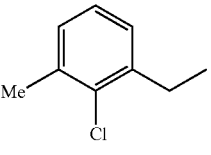 | MS(ESI) m/z: 317(M+H)+; 1H-NMR(300 MHz, DMSO-d6) δ 2.34(3H, s), 4.10(1H, s), 5.38(1H, s), 7.20-7.39(3H, m), 8.73(1H, s), 9.25(1H, s), 11.17(1H, s), 12.91(1H, s). |
|---|---|---|---|
| 56 | 55 | 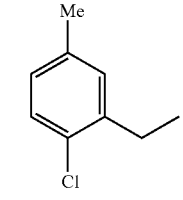 | MS(ESI) m/z: 317(M+H)+; 1H-NMR(300 MHz, DMSO-d6) δ 4.08(2H, s), 5.56(1H, s), 7.12(1H, dd), 7.23(1H, s), 7.33 (1H, d), 8.85(1H, s), 9.24(1H, s), 11.63(1H, s), 13.29(1H, s). |
| 57 | 1 | 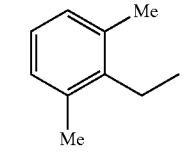 | MS(ESI) m/z: 297(M+H); 1H-NMR(300 MHz, DMSO-d6) δ 2.26(6H, s), 3.96(2H, s), 4.98(1H, s), 7.00-7.07(3H, m), 8.23(1H, s), 9.18(1H, s), 10.32(1H, s), 12.24(1H, s). |
| 58 | 1 | 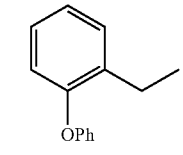 | MS(ESI) m/z: 361(M+H); 1H-NMR(300 MHz, DMSO-d6) δ 3.98(2H, s), 5.14(1H, s), 6.83-6.90(3H, m), 7.00-7.20(2H, m), 7.27-7.35(3H, m), 7.43(1H, d, J=10.2 Hz), 8.60(1H, s), 9.18(1H, s), 10.92(1H, s), 12.64(1H, s). |
| 59 | 1 | 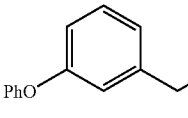 | MS(ESI) m/z: 361(M+H); 1H-NMR(300 MHz, DMSO-d6) δ 3.92(2H, s), 5.36(1H, s), 6.89(1H, d, J=10.5 Hz), 7.00-7.07(3H, m), 7.11-7.19(2H, m), 7.36-7.43(3H, m), 8.80(1H, s), 9.24(1H, s), 11.20(1H, s), 13.00(1H, s). |
| 60 | 1 | 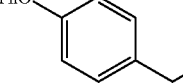 | MS(ESI) m/z: 361(M+H); 1H-NMR(300 MHz, DMSO-d6) δ 3.92(2H, s), 5.40(1H, s), 6.98-7.03(4H, m), 7.12-7.17(1H, m), 7.36-7.43(4H, m), 8.88(1H, s), 9.27(1H, s), 11.38(1H, s), 13.11(1H, s). |

TABLE 7-continued

| 61 | 1 | 4-Ph-C6H4- | MS(ESI) m/z: 331(M+H); 1H-NMR(300 MHz, DMSO-d6) δ 5.30(1H, s), 7.48-7.53(2H, m), 7.77-7.83(3H, m), 7.96(2H, d, J=10.5 Hz), 8.13(2H, d, J=10.5 Hz), 8.58(1H, s), 9.31(1H, s), 10.53(1H, s), 12.23(1H, s). |
| --- | --- | --- | --- |
| 62 | 1 | 4-MeO-C6H4- | MS(ESI) m/z: 285(M+H); 1H-NMR(300 MHz, DMSO-d6) δ 3.83(3H, s), 5.31(1H, s), 7.16(2H, d, J=10.5 Hz), 8.11(2H, d, J=10.5 Hz), 8.28(1H, s), 9.24(1H, s), 10.60(1H, s), 12.04(1H, s). |
| 63 | 1 | 3-NO2-C6H4- | MS(ESI) m/z: 300(M+H); 1H-NMR(300 MHz, DMSO-d6) δ 5.20(1H, s), 7.80-7.87(1H, m), 8.50-8.79(3H, m), 8.92(1H, s), 9.30(1H, s), 10.40(1H, s), 12.38(1H, s). |

TABLE 8

| 64 | 1 | 4-O2N-C6H4- | MS(ESI) m/z: 300(M+H); 1H-NMR(300 MHz, DMSO-d6) δ 5.25(1H, s), 6.89(1H, d, J=10.5 Hz), 8.38(2H, d, J=10.2 Hz), 8.44(2H, d, J=10.2 Hz), 8.60(1H, s), 9.27(1H, s), 10.60(1H, s), 12.48(1H, s). |
| --- | --- | --- | --- |
| 65 | 11 | 4-HO-2-Cl-C6H3-CH2- | MS(ESI) m/z: 319(M+H)+; 1H-NMR(300 MHz, DMSO-d6) δ 3.86(2H, s), 4.91(1H, s), 6.70(1H, dd), 6.82(1H, s), 7.17(1H, d), 8.30(1H, s), 9.14(1H, s), 10.31(1H, s), 12.19(1H, s). |
| 66 | 11 | 3,4-(HO)2-2-Cl-C6H2-CH2- | MS(ESI) m/z: 335(M+H)+; 1H-NMR(300 MHz, DMSO-d6) δ 3.90(2H, s), 5.18(1H, s), 6.60-6.72(2H, m), 8.65(1H, s), 9.21(1H, s), 11.02(1H, s). |
| 67 | 38 | 5-OMe-2-Cl-C6H3-CH2- | MS(ESI) m/z: 333(M+H)+; 1H-NMR(300 MHz, DMSO-d6) δ 3.74(3H, s), 4.09(2H, s), 5.57(1H, s), 6.89(1H, dd), 7.06(1H, s), 7.35(1H, d), 8.93(1H, s), 9.27(1H, s), 11.62(1H, s), 13.41(1H, s). |
| 68 | 11 | 5-OH-2-Cl-C6H3-CH2- | MS(ESI) m/z: 319(M+H)+ |
| 69 | 1 | sec-butyl (CHMe2CH-) | MS(ESI) m/z: 235(M+H)+ |
| 70 | 1 | cyclopropyl-CH2- | MS(ESI) m/z: 233(M+H)+ |

TABLE 8-continued
| 71 | 38 | 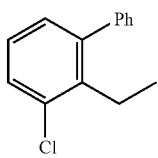 | MS(ESI) m/z: 379(M+H)+; 1H-NMR(300 MHz, DMSO-d6) δ 4.01(2H, s), 5.39(1H, s), 7.23-7.52(8H, m), 8.93(1H, s), 9.28(1H, s), 11.53(1H, s), 13.09(1H, s). |
TABLE 9
| 72 | 1 | 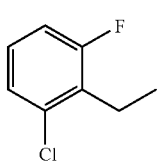 | MS(ESI) m/z: 321(M+H)+; 1H-NMR(300 MHz, DMSO-d6) δ 4.07(2H, s), 4.93(1H, s), 7.24-7.43(4H, m), 8.25(1H, s), 9.15(1H, s), 10.29(1H, s), 12.36(1H, s). |
| 73 | 38 | 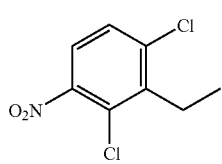 | MS(ESI) m/z: 382(M+H)+; 1H-NMR(300 MHz, DMSO-d6) δ 4.34(2H, s), 5.05(1H, s), 7.80(1H, d), 8.04(1H, d), 8.43(1H, s), 9.17(1H, s), 10.63(1H, s), 12.76(1H, s). |
| 74 | — | 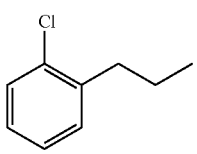 | MS(ESI) m/z: 317(M+H)+ |
| 75 | 38 | 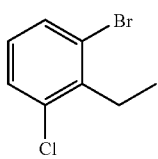 | MS(ESI) m/z: 382(M+H)+ |
| 76 | 38 | 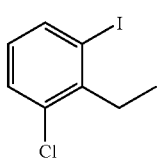 | MS(ESI) m/z: 429(M+H)+; 1H-NMR(300 MHz, DMSO-d6) δ 4.40(2H, s), 5.55(1H, s), 7.09(1H, dd), 7.54(1H, d), 7.89 (1H, s), 8.98(1H, s), 9.30(1H, s), 11.62(1H, s), 13.42(1H, s). |
| 77 | — | 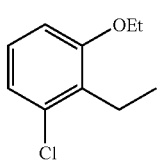 | MS(ESI) m/z: 347(M+H)+ |
| 78 | 55 | 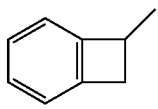 | MS(ESI) m/z: 281(M+H)+; 1H-NMR(300 MHz, DMSO-d6) δ 3.44-3.78(2H, m), 4.59(1H, s), 5.14(1H, s), 7.12-7.28(4H, m), 8.56(1H, s), 9.21(1H, s), 10.74(1H, s), 12.53(1H, s). |
| 79 | 55 | 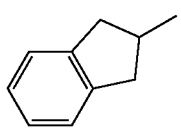 | MS(ESI) m/z: 295(M+H)+; 1H-NMR(300 MHz, DMSO-d6) δ 3.24-3.33(4H, m), 5.32(1H, s), 7.11-7.27(4H, m), 8.88(1H, s), 9.27(1H, s), 11.16(1H, s), 12.77(1H, s). |

TABLE 9-continued

| 80 | — | 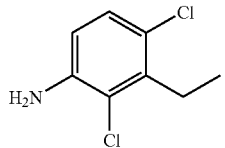 | MS(ESI) m/z: $_{380}$(M+H)+; 1H-NMR(300 MHz, DMSO-d6) δ 2.69(6H, s), 4.22(2H, s), 5.01(1H, s), 7.15(1H, d), 7.40 (1H, d), 8.40(1H, s), 9.17(1H, s), 10.57(1H, s), 12.50(1H, s). |

TABLE 10

| 81 | 1 | 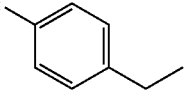 | MS(ESI) m/z: $_{297}$(M+H)+; 1H-NMR(300 MHz, DMSO-d6) δ 1.15(3H, t, J=7.8 Hz), 2.57(2H, q, J=7.8 Hz), 3.82(2H, s), 5.11(1H, s), 7.18(2H, d, J=8.1 Hz), 7.25(2H, d, J=8.1 Hz), 8.58(1H, brs), 9.20(1H, brs), 10.72(1H, brs), 12.58(1H, brs). |
| 82 | 1 | 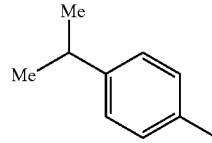 | MS(ESI) m/z: $_{311}$(M+H)+; 1H-NMR(300 MHz, DMSO-d6) δ 1.18(6H, d, J=6.9 Hz), 2.86(1H, m), 3.85(2H, s), 5.25(1H, s), 7.20-7.28(4H, m), 8.72(1H, brs), 9.23(1H, brs), 11.00(1H, brs), 12.83(1H, brs). |
| 83 | 43 | 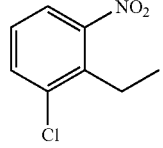 | MS(ESI) m/z: $_{348}$(M+H)+ |
| 84 | — | 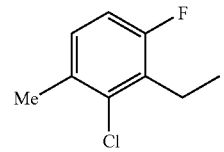 | MS(ESI) m/z: $_{335}$(M+H)+; 1H-NMR(300 MHz, DMSO-d6) δ 2.21(3H, s), 4.17(2H, s), 5.64(1H, s), 7.21-7.36(2H, m), 8.97 (1H, s), 9.28(1H, s), 11.77(1H, s), 13.63(1H, s). |
| 85 | 84 | 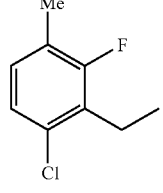 | MS(ESI) m/z: $_{335}$(M+H)+; 1H-NMR(300 MHz, DMSO-d6) δ 2.30(3H, s), 4.12(2H, s), 5.28(1H, s), 7.18(1H, dd), 7.36 (1H, dd), 8.64(1H, s), 9.21(1H, s), 11.10(1H, s), 12.98(1H, s). |
| 86 | 84 | 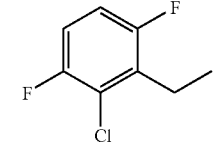 | MS(ESI) m/z: $_{339}$(M+H)+; 1H-NMR(300 MHz, DMSO-d6) δ 4.12(2H, s), 5.11(1H, s), 7.28-7.51(2H, m), 8.46(1H, s), 9.18(1H, s), 10.75(1H, s), 12.77(1H, s). |
| 87 | 1 | 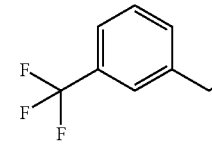 | MS(ESI) m/z: $_{337}$(M+H)+; 1H-NMR(300 MHz, DMSO-d6) δ 4.03(2H, s), 5.16(1H, s), 7.57-1.77(4H, m), 8.63(1H, brs), 9.23(1H, brs), 10.86(1H, brs), 12.76(1H, brs). |
| 88 | 1 | 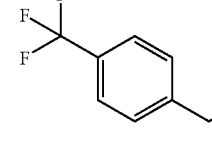 | MS(ESI) m/z: $_{337}$(M+H)+; 1H-NMR(300 MHz, DMSO-d6) δ 3.96(2H, s), 4.91(1H, s), 7.56(1H, d, J=8.1 Hz), 7.72(1H, d, J=8.1 Hz), 8.37(1H, brs), 9.17(1H, brs), 10.31(1H, brs), 12.29(1H, brs). |

TABLE 10-continued

| 89 | 1 | (3-iodobenzyl structure) | MS(ESI) m/z: $_{395}$(M+H)+; 1H-NMR(300 MHz, DMSO-d6) δ 3.90(2H, s), 5.27(1H, s), 7.13-7.19(1H, m), 7.36-7.39(1H, m), 7.64-7.67(1H, m), 7.75-7.78(1H, m), 8.76(1H, brs), 9.25 (1H, brs), 11.08(1H, brs), 12.90(1H, brs). |
|---|---|---|---|

TABLE 11

| 90 | 1 | (4-fluorobenzyl structure) | MS (ESI) m/z: $_{287}$ (M+H)+; 1H-NMR (300 MHz, DMSO-d6) δ 3.85(2H, s), 4.99(1H, s), 7.14-7.22(2H, m), 7.34-7.40 (2H, m), 8.45(1H, brs), 9.18(1H, brs), 10.48(1H, brs), 12.40(1H, brs). |
|---|---|---|---|
| 91 | 1 | (3-nitrobenzyl structure) | MS (ESI) m/z: $_{314}$ (M+H)+ |
| 92 | 1 | (4-nitrobenzyl structure) | MS (ESI) m/z: $_{314}$ (M+H)+ |
| 95 | 1 | (tolyl structure) | MS (ESI) m/z: $_{269}$ (M+H)+ |
| 96 | 1 | (tert-butyl structure) | MS (ESI) m/z: $_{235}$ (M+H)+ |

EXPERIMENTAL EXAMPLES

Experimental Example 1

Test of Production or Inhibition of Production of TNF-α from Mouse Peritoneal Macrophage Peritoneal cells were recovered from the peritoneal cavity of ICR mice (male, 5- to 7-week-old, Charles River Japan, Inc.), and plated on a 96-well half plate (Costar3696) at $1 \times 10^5$ cells per well. As the medium, RPMI-1640 containing 10% bovine calf serum was used and each reagent was prepared using the medium. Mouse GM-CSF (Peprotech) and mouse IFN-γ (Peprotech) were added at each final concentration of 10 ng/ml, lipopolysaccharide (E. coli 0111: B4 LPS, DIFCO, lot 99078) was added at a final concentration of 5 ng/ml and the compound of the present invention was added in a 3-fold dilution, 8 step dilution series from a final concentration of 300 μM, and the cells were cultured for 16 hr. The concentration of TNF-α secreted in the culture supernatant was determined by measuring absorbance at 450 nm on a V-max kinetic microplate reader (Molecular Devices) using a mouse TNF-α ELISA quantitative determination kit (#2673KI manufactured by Pharmingen). As a result, the compound group of the present invention decreased the amount of TNF-α produced by the stimulation with lipopolysaccharide.

Experimental Example 2

Efficacy Test Using Rat Adjuvant Arthritis

According to a conventional method, light mineral oil (50 μl, SIGMA) containing 3 mg/ml of M. tuberculosis dead cells (DIFCO, lot 165308) was subcutaneously injected to the sole of the left hindpaw of LEWIS rats (female, 7-week-old, Charles River Japan, Inc.) to induce onset of arthritis. The test compound in 100% polyethylene glycol (molecular weight 400, SIGMA) as an administration vehicle was forcibly administered orally to 4 rats per group. The test compound (Example compound 3) was administered 3 times a day at a dose of 40 mg/kg body weight and 120 mg/kg body weight for 3 days from 24 hr after induction of the onset. As the index of arthritis, changes in the volume of hindpaw were measured. The hindpaw volume was measured using a volume meter TK-105 (UNICOM, Japan) for water immersion volume up to hindpaw hairline, and compared with the measured value at the start of the administration (24 hr after onset induction), which was taken as 0. By the administration of the compound of the present invention, swelling of the joint was remarkably suppressed.

The results are shown in FIG. 1.

INDUSTRIAL APPLICABILITY

The compound group represented by the formula (I) of the present invention has a superior TNF-α production inhibitory action, and further superior efficacy against chronic inflammation pathology. Therefore, it is useful for the prophylaxis or treatment of various diseases caused by abnormal production of TNF-α.

The invention claimed is:

1. A heterocyclic compound represented by the formula (I)

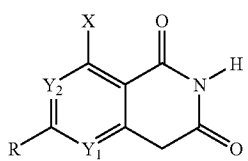

or a tautomer thereof, or a pharmaceutically acceptable salt thereof,
wherein R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s),
a heterocyclic-alkyl group optionally having substituent(s),
A-B-
wherein A is:
an alkyl group optionally having substituent(s),
a cycloalkyl group optionally having substituent(s),
an aryl group optionally having substituent(s),
a heteroaryl group optionally having substituent(s) or
a heterocyclic group optionally having substituent(s), and
B is an oxygen atom or a sulfur atom, and

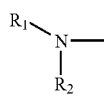

wherein $R_1$ and $R_2$ are the same or different and each is:
a hydrogen atom,
an alkyl group optionally having substituent(s),
a cycloalkyl group optionally having substituent(s),
an aryl group optionally having substituent(s),
a heteroaryl group optionally having substituent(s) or
a heterocyclic group optionally having substituent(s),
X is an amino group optionally having substituent(s); and
$Y_1$ and $Y_2$ is each a nitrogen atom or a —CH— moiety provided that $Y_1$ and $Y_2$ are not carbon atoms at the same time.

2. The heterocyclic compound of claim 1 or a tautomer thereof, or a pharmaceutically acceptable salt thereof, wherein, in the formula (I), $Y_1$ and $Y_2$ are nitrogen atoms.

3. The heterocyclic compound of claim 1 or a tautomer thereof, or a pharmaceutically acceptable salt thereof, wherein, in the formula (I), R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s), and
a heterocyclic-alkyl group optionally having substituent(s).

4. The heterocyclic compound of claim 1 or a tautomer thereof, or a pharmaceutically acceptable salt thereof, wherein, in the formula (I), R is any of:
an alkyl group optionally having substituent(s),
a cycloalkyl group optionally having substituent(s),
a cycloalkylalkyl group optionally having substituent(s),
an aryl group optionally having substituent(s),
an aralkyl group optionally having substituent(s),
a heteroaryl group optionally having substituent(s),
a heteroarylalkyl group optionally having substituent(s),
a heterocyclic group optionally having substituent(s), and
a heterocyclic-alkyl group optionally having substituent(s); and
$Y_1$ and $Y_2$ are nitrogen atoms.

5. The heterocyclic compound of claim 1 or a tautomer thereof, or a pharmaceutically acceptable salt thereof, wherein, in the formula (I), R is any of:
an alkyl group optionally having substituent(s),
a cycloalkylalkyl group optionally having substituent(s),
an aryl group optionally having substituent(s),
an aralkyl group optionally having substituent(s) and
a heteroarylalkyl group optionally having substituent(s).

6. The heterocyclic compound of claim 1 or a tautomer thereof, or a pharmaceutically acceptable salt thereof, wherein, in the formula (I), R is any of:
an alkyl group optionally having substituent(s),
a cycloalkylalkyl group optionally having substituent(s),
an aryl group optionally having substituent(s),
an aralkyl group optionally having substituent(s) and
a heteroarylalkyl group optionally having substituent(s); and
$Y_1$ and $Y_2$ are nitrogen atoms.

7. The heterocyclic compound of claim 1 or a tautomer thereof, or a pharmaceutically acceptable salt thereof, wherein, in the formula (I), R is any of:
an alkyl group optionally having substituent(s),
a cycloalkylalkyl group optionally having substituent(s),
an aryl group optionally having substituent(s),
an aralkyl group optionally having substituent(s) and
a heteroarylalkyl group optionally having substituent(s);
$Y_1$ and $Y_2$ are nitrogen atoms; and
X is an amino group.

8. The heterocyclic compound of claim 1 or a tautomer thereof, or a pharmaceutically acceptable salt thereof, wherein, in the formula (I),
R is an aralkyl group optionally having substituent(s);
$Y_1$ and $Y_2$ are nitrogen atoms; and
X is an amino group.

9. A pharmaceutical composition comprising:
a heterocyclic compound of claim 1, or a tautomer thereof, or a pharmaceutically acceptable salt thereof, as an active ingredient; and
a pharmacologically acceptable carrier.

10. A pharmaceutical composition for the treatment of at least one disease selected from the group consisting of Crohn's disease, ulcerative colitis, sepsis, and rheumatoid arthritis, comprising a therapeutically effective amount of the compound of claim 1 and a pharmacologically acceptable carrier.

11. A method of treating at least one disease selected from the group consisting of Crohn's disease, ulcerative colitis, sepsis, and rheumatoid arthritis, comprising: administering, to a patient in need thereof, an effective amount of the heterocyclic compound of claim 1, or a tautomer thereof, or a pharmaceutically acceptable salt thereof.

12. A kit comprising a pharmaceutical composition comprising a therapeutically effective amount of the composition of claim 9 and a package, wherein the pharmaceutical composition is contained in the package.

13. The kit of claim 12, further comprising instructions for the use of said pharmaceutical composition, wherein the instructions are contained in the package.

* * * * *